US007585644B2

(12) United States Patent
Slater et al.

(10) Patent No.: US 7,585,644 B2
(45) Date of Patent: Sep. 8, 2009

(54) MYCOPOLASMA DETECTING METHODS AND MATERIALS

(75) Inventors: Kevin John Slater, Nottingham (GB); Anthony Pitt, Nottingham (GB); Anne Cox, Nottingham (GB); Sharon Patricia Mary Crouch, Nottingham (GB)

(73) Assignee: Cambrex Bio Science Nottingham, Ltd., Nottingham (GB)

( * ) Notice: Subject to any disclaimer, the term of this patent is extended or adjusted under 35 U.S.C. 154(b) by 764 days.

(21) Appl. No.: 10/825,607

(22) Filed: Apr. 16, 2004

(65) Prior Publication Data

US 2004/0265942 A1 Dec. 30, 2004

Related U.S. Application Data

(60) Provisional application No. 60/463,323, filed on Apr. 17, 2003.

(30) Foreign Application Priority Data

Apr. 17, 2003 (GB) ................................ 0308829.1

(51) Int. Cl.
 C12Q 1/50 (2006.01)
(52) U.S. Cl. ......................................................... 435/17
(58) Field of Classification Search ........................ None
 See application file for complete search history.

(56) References Cited

U.S. PATENT DOCUMENTS

| 5,330,906 | A | 7/1994 | Kajiyama et al. |
| 5,374,534 | A | 12/1994 | Zomer et al. |
| 5,583,024 | A | 12/1996 | McElroy et al. |
| 5,876,995 | A | 3/1999 | Bryan |
| 6,004,767 | A | 12/1999 | Crouch et al. |
| 6,074,859 | A | 6/2000 | Hirokawa et al. |
| 6,436,682 | B1 | 8/2002 | Bryan et al. |

FOREIGN PATENT DOCUMENTS

| EP | 0 301 541 | 2/1989 |
| EP | 0 353 464 | 2/1990 |
| EP | 0 449 621 | 8/1996 |
| GB | 2 323 167 | 6/1999 |
| GB | 2 357 336 | 12/2001 |
| WO | WO 94/17202 | 8/1994 |
| WO | WO 95/18853 | 7/1995 |
| WO | WO 96/22376 | 7/1996 |
| WO | WO 98/46729 | 10/1998 |
| WO | WO 99/02697 | 1/1999 |
| WO | WO 99/16896 | 4/1999 |
| WO | WO 99/37799 | 7/1999 |
| WO | WO 99/41408 | 8/1999 |
| WO | WO 00/24878 | 5/2000 |
| WO | WO 00/70082 | 11/2000 |
| WO | WO 01/31028 | 5/2001 |

OTHER PUBLICATIONS

Ito et al. Analytic Sciences 2003;19:105-109.*
Ingram-Smith et al. Trends in Microbiology 2006;14(6):249-253.*
Cordwell, et al., "Characterisation of basic proteins from *Spiroplasma melliferum* using novel immobilised pH gradients", Electrophoresis vol. 18, 1997; pp. 1393-1398.
Zhu, et al., "Sequence and organization of genes encoding enzymes involved in pyruvate metabolism in *Mycoplasma capricolum*", Protein Science vol. 5. 1996; pp. 1719-1736.
Razin et al., "Molecular Biology and Pathogenicity of Mycoplasmas", *Microbiology and Molecular Biology Reviews*, Dec. 1998, p. 1094-1156.
Rottem et al., "Beware of Mycoplasmas", *TIBTECH*, Apr. 1993, vol. 11, p. 143-151.
Rottem, "Sterols and Acylated Proteins in Mycoplasmas", *Biochecmical and Biophysical Research Communications*, 2002, vol. 292, p. 1289-1292.
Raab, "Cultural Revolution: Mycoplasma Testing Kits and Services", *The Scientist*, vol. 13(20), Oct. 11, 1999, www.the-scientist.com.
Daxboeck et al., "Laboratory Diagnosis of *Mycoplasma pneumoniae* infection", *Clinical Microbiology and Infection*, vol. 9(4), Apr. 2003, p. 262-273.
Masuda et al, "Cloning and sequence analysis of cDNA for luciferase of a Japanese firefly, *Luciola cruciata*", *Gene*, vol. 77, 1989, p. 265-270.
Baseman et al., "Mycoplasmas: Sophisticated, Reemerging, and Burdened by Their Notoriety" *Emerging Infectious Diseases*, vol. 3(1), Jan.-Mar. 1997, p. 21-32.
Kirchoff et al., "*Mycoplasma crocodyli* sp. nov., a New Species from Crocodiles", *International Journal of Systematic Bacteriology*, Jul. 1997, p. 742-746.
Taylor et al., "Diversity of energy-yielding substrates and metabolism in avian mycoplasmas", *Veterinary Microbiology*, vol. 51, 1996, p. 291-304.
"Cell Culture Contamination Example: Mycoplasma", www.unc.edu/depts/tcf/mycoplasma.htm.
Duffy et al., "Comparative potency of gemifloxacin, new quinolones, macrolides, tetracycline and clindamycin against *Mycoplasma* spp.", *Journal of Antimicrobial Chemotherapy*, vol. 45(Suppl. S1), 2000, p. 29-33.
Taylor-Robinson et al., "Antibiotic susceptibilities of mycoplasmas and treatment of mycoplasmal infections", *Journal of Antimicrobial Chemotherapy*, vol. 40, 1997, p. 622-630.
Uphoff et al., "Elimination of mycoplasma from leukemia-lymphoma cell lines using antibiotics", *Leukemia*, vol. 16, 2002, p. 284-288.
Muhlrad et al., "Acetate Kinase Activity in Mycoplasmas", *Journal of Bacteriology*, vol. 147(1), Jul. 1981, p. 271-273.

(Continued)

*Primary Examiner*—Jon P Weber
*Assistant Examiner*—Bin Shen
(74) *Attorney, Agent, or Firm*—Banner & Witcoff, Ltd.

(57) ABSTRACT

The invention relates to a method of detecting the presence of mycoplasma in a test sample comprising:
(i) providing a test sample; and
(ii) detecting and/or measuring the activity of acetate kinase and/or carbamate kinase in the test sample, the activity being indicative of contamination by mycoplasma.

45 Claims, 10 Drawing Sheets

OTHER PUBLICATIONS

Figure 1:
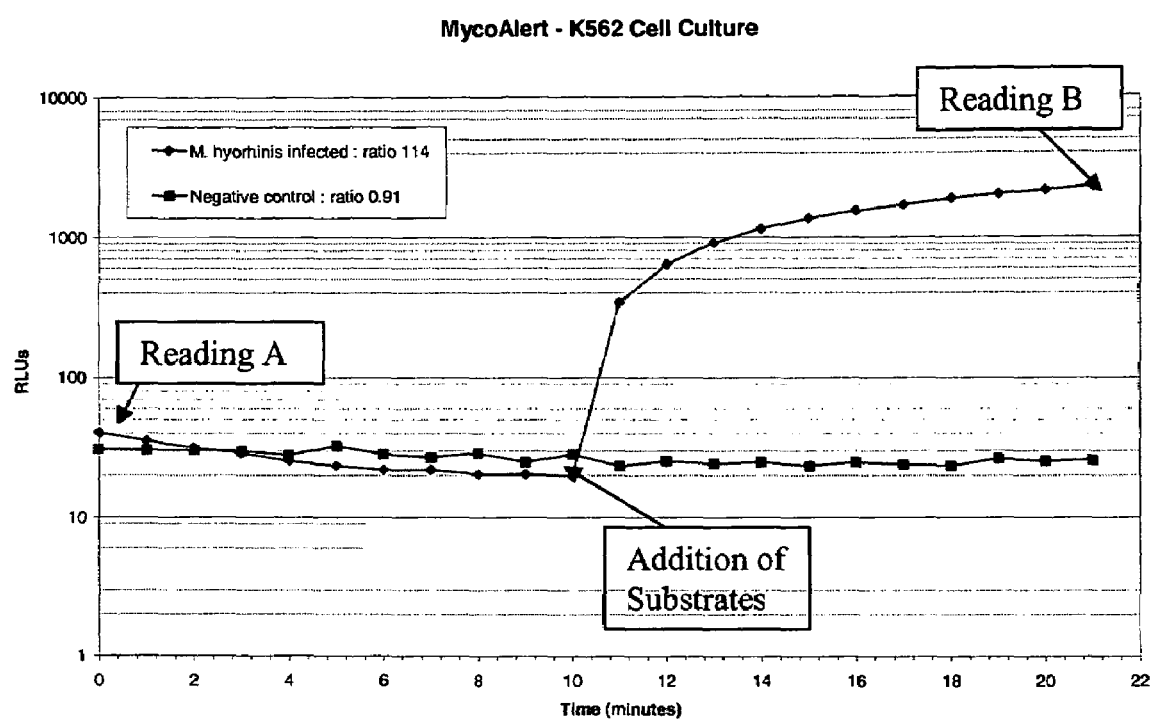

Kahane et al., "Possible Role of Acetate Kinase in ATP Generationi of *Mycoplasma hominis* and *Acholeplasma laidlawii*", *FEMS Microbiology Letters*, vol. 3, 1978, p. 143-145.

Kahane et al., "Purification of Properties of Acetate Kinase from *Acholeplasma laidawii*", *Journal of Bacteriology*, Feb 1979, p. 764-772.

Limb et al., "Antimicrobial susceptibility testing of mycoplasmas by ATP bioluminescence", *J. Med. Microbiol.*, vol. 35, 1991, p. 89-92.

Saglio et al., "ATP and Energy Charge as Criteria of Growth and Metabolic Activity of Mollicutes: Application to *Spiroplasma citri*", *Journal of General Microbiology*, vol. 110, 1979, p. 13-20.

Bachy et al., "Beta galactosidase release as an alternative to chromium release in cytotoxic T-cell assays", *Journal of Immunological Methods*, vol. 230, 1999, p. 37-46.

Nociari et al., "A novel one-step, highly sensitive fluorometric assay to evaluate cell-mediated cytotoxicity", *Journal of Immunological Methods*, vol. 213, 1998, p. 157-167.

Curt, "Cancer Drug Development: New Targets for Cancer Treatment", *The Oncologist*, vol. 1, 1996, p. ii-iii.

Squirrell, "Firefly Luciferase", *Journal of Defence Science*, vol. 2(3), p. 291-297.

Karp et al., "A streptavidin-luciferase fusion protein: comparisons and applications", *Biomolecular Engineering*, vol. 16, 1999, p. 101-104.

Golding et al., "Adjustment of $K'$ to Varying pH and pMg for the Creatine Kinase, Adenylate Kinase and ATP Hydrolysis Equilibria Permitting Quantitative Bioenergetic Assessment", *The Journal of Experimental Biology*, vol. 198, 1995, p. 1775-1782.

Teague et al., "Adjustment of $K'$ for the Creatine Kinase, Adenylate Kinase and ATP Hydrolysis Equilibria to Varying Temperature and Ionic Strength", *The Journal of Experimental Biology*, col. 199, 1996, p. 509-512.

Feutren et al., "Immune Lysis of Hepatocytes in Culture: Accurate Detection by Asparate Aminotransferase Release Measurement", *Journal of Immunilogical Methods*, vol. 75, 1984, p. 85-94.

D'Atri et al., "A Miniaturized Cell-Mediated Cytotoxicity Assay with Human Effector Mononuclear Cells", *Int. J. Tiss. Reac.*, vol. VIII(5), 1986, p. 383-390.

Kasatori et al., "Cytotoxicity Test Based on Luminescent Assay of Alkaline Phosphate Released from Target Cells", *Rinsho Byori*, vol. 42, 1994, p. 1050-1054.

Decker et al., "A quick and simple method for the quantitation of lactate dehydrogenase release in measurements of cellular cytotoxicity and tumor necrosis factor (TNF) activity", *Journal of Immunological Methods*, vol. 15, 1988, p. 61-69.

Branchini et al., "Site-Directed Mutagenesis of Firefly Luciferase Active Site Amino Acids: A Proposed Model for Bioluminescence Color", *Biochemistry*, vol. 38, 1999, p. 13223-13230.

Cohen et al., "A Microchip-Based Enzyme Assay for Protein Kinase A", *Analytical Biochemistry*, vol. 273, 1999, p. 89-97.

Eu et al., "Homogenous Bioluminescence Assay for Galactosuria: Interface and Kinetic Analysis", *Analytical Biochemistry*, vol. 271, 1999, p. 168-176.

Lehel et al., "A Chemiluminescent Microtiter Plate Assay for Sensitive Detection of Protein Kinase Activity", *Analytical Biochemistry*, vol .244, 1997, p. 340-346.

Thore, "Technical Aspects of Bioluminescent Firefly Luciferase Assat of ATP", *Science Tools*, vol. 26(2), 1979, p. 30-35.

Olsson et al., "Leakage of Adenylate Kinase From Stored Blood Cells", *Journal of Applied Biochemistry*, vol. 5, 1983, p. 437-445.

Sala-Newby et al., "Engineering firefly luciferase as an indicator of cyclic AMP-dependent protein kinase in living cells", *FEBS*, vol. 307(2), p. 241-244.

Pastorino et al., "Functional Consequences of the Sustained or Transient Activation by Bax of the Mitochondrial Permeability Transition Pore", *The Journal of Biological Chemistry*, vol. 274(44), Oct. 1999, p. 31734-31739.

Tatsumi et al., "Construction of Biotinylated Firefly Luciferases Using Biotin Acceptor Peptides", *Analytical Biochemistry*, vol. 243, 1996, p. 176-180.

Branchini et al., "The Role of Lysine 529, a Conserved Residue of the Acyl-Adenylate-Forming Enzyme Superfamily, in Firefly Luciferase", *Biochemistry*, vol. 39, 2000, p. 5433-5440.

White et al., "Improved thermostability of the North American firefly luciferase: saturation mutagenesis at position 354", *Biochem. J.*, vol. 319, 1996, p. 343-350.

Devine et al., "Luciferase from the East European firefly *Luciola mingrelica*: cloning and nucleotide sequence of the cDNA, overexpression in *Escherichia coil* and purification of the enzyme", *Biochimica et Biophysica Acta*, vol. 1173, 1993, p. 121-132.

Tully et al., "*Acholeplasma brassicae* sp. nov. and *Acholeplasma palmae* sp. nov., Two Non-Sterol-Requiring Mollicutes from Plant Surfaces", *International Journal of Systematic Bacteriology*, vol. 44(4), Oct. 1994, p. 680-684.

Forsyth et al., "*Mycoplasma sturni* sp. nov., from the Conjunctiva of a European Starling (*Sturnus vulgaris*)", *International Journal of Systematic Bacteriology*, vol. 46(3), Jul. 1996, p. 716-719.

Garraud et al., "Effect of Blood Storage on Lymphocyte Subpopulations", *Journal of Immunological Methods*, vol. 75, 1984, p. 95-98.

McGarrity et al., "Cell Culture Mycoplasmas", *The Mycoplasmas*, vol. IV, 1985, p. 353-390.

Battaglia et al., "Hoechst 33258 Staining for Detecting Mycoplasma Contamination in Cell Cultures: a Method for Reducing Fluorescence Photobleaching", *Biotechnic & Histochemistry*, vol. 69(3), 1994, p. 152-156.

Whitaker et al., "A Rapid and Sensitive Method for the Detection of Mycoplasmas in Infected Cell Cultures Using 6-Methyl Purine Deoxyriboside", *Develop. Biol. Standard*, vol. 68, 1957, p. 503-509.

Verhoef et al., "Adenosine Phosphorylase Activity in Mycoplasma-free Growth Media for Mammalian Cells", *Experimental Cell Research*, vol. 149, 1983, p. 37-44.

De Wet et al., "Firefly Luciferase Gene: Structure and Expression in Mammalian Cells", *Molecular and Cellular Biology*, Feb. 1987, p. 725-737.

De Wet et al., "Cloning Firefly Luciferase", *Methods in Enzymology*, vol. 133, p. 3-14.

Wood et al., "Complementary DNA Coding Click Beetle Luciferases Can Elicit Bioluminescence of Different Colors", *Science*, vol. 244, p. 700-702.

Schram et al., "Improved ATP Methodology for Biomass Assays", *Journal of Bioluminescence and Chemiluminescence*, vol. 4, 1989, p. 390-398.

Stanley et al., "A Review of Bioluminescent ATP Techniques in Rapid Microbiology", *Journal of Bioluminescence and Chemiluminescence*, vol. 4, 1989, p. 375-380.

Pellegrini et al., "Bactericidal activities of lysozyme and aprotinin against Gram-negative and Gram-positive bacteria related to their basic character", *Journal of Applied Bacteriology*, vol. 72, 1992, p. 180-187.

\* cited by examiner

MYCOPOLASMA DETECTING METHODS AND MATERIALS

This application claims the benefit under 35 U.S.C. § 119 (e)(1) of prior filed provisional application 60/463,323 filed Apr. 17, 2003.

The present invention relates to assay methods and materials for detecting members of the Mollicutes family, that contaminate a test sample, such as a sample from a cell culture.

Taxonomically, the lack of cell walls has been used to separate Mollicutes from other bacteria in a class named Mollicutes (Razin et al 1998). The members of this class are summarised in the following table 1.

TABLE 1

Major Characteristics and Taxonomy of the Class Mollicutes.

| Classification | No. Species | Genome Size (kb) | Mol % G + C of genome | Habitat |
|---|---|---|---|---|
| Order I: *Mycoplasmatales* | | | | |
| Family I: *Mycoplasmataceae* | | | | |
| Genus I: *Mycoplasma* | 102 | 580-1,350 | 23-40 | Humans, animals |
| Genus II: *Ureaplasma* | 6 | 760-1,170 | 27-30 | Humans, animals |
| Order II: *Entoplasmatales* | | | | |
| Family I: *Entoplasmataceae* | | | | |
| Genus I: *Entomoplasma* | 5 | 790-1,140 | 27-29 | Insects, plants |
| Genus II: *Mesoplasma* | 12 | 870-1,100 | 27-30 | Insects, plants |
| Family II: *Spiroplasmataceae* | | | | |
| Genus I: *Spiroplasma* | 33 | 780-2,220 | 24-31 | Insects, plants |
| Order III: *Acholeplasmatales* | | | | |
| Family I: *Acholeplasmataceae* | | | | |
| Genus: *Acholeplasma* | 13 | 1,500-1,650 | 26-36 | Animals, some plants, insects |
| Order IV: *Anaeroplasmatales* | | | | |
| Family: *Anaeroplasmataceae* | | | | |
| Genus I: *Anaeroplasma* | 4 | 1,500-1,650 | 29-34 | Bovine/ovine rumen |
| Genus II: *Asteroplasma* | 1 | 1,500 | 40 | Bovine/ovine rumen |
| Undefined (1999) | | | | |
| Phytoplasma | | 640-1,185 | 23-29 | Insects, plants |

In the context of the present application, the term "mycoplasma" is intended to embrace all members of the class Mollicutes, not just Mycoplasmatales. In fact, "mycoplasma" is the common term in the art for all of the Mollicutes.

Mycoplasmas are widespread in nature as parasites of humans, mammals, reptiles, fish, arthropods and plants. They are the smallest and simplest prokaryotes. They lack a rigid cell wall and are incapable of peptidoglycan synthesis; they are therefore not sensitive to antibiotics, such as penicillin and its analogues. *Mycoplasma* have developed by degenerate evolution from gram-positive bacteria with a low molecular percentage guanine and cytosine content of DNA ie. the *Lactobacillus, Bacillus, Streptococcus* and two *Clostridium* species. The Mollicutes have lost, during the process of evolution, a substantial part of their genetic information. It is this limited coding capacity that has dictated the need for a parasitic way of life. Most species are facultative anaerobes, but some are obligate, and hence the similarities in their metabolism to anaerobic bacteria.

More than 180 Mollicute species have been identified of which 20 distinct *Mycoplasma* and *Acholeplasma* species from human, bovine and swine have been isolated from cell culture. There are six species that account for 95% of all mycoplasma infections; these are *M. orale, M. arginii, M. fermentans, M. salivarum, M. hyorhinis* and *A. laidlawii*. The major cause of infection is cross contamination from other cell lines introduced into laboratories. Also an unwanted source of exogenous mycoplasma can be found in tissue culture reagents, such as serum products. *Mycoplasma*, unlike bacterial, contamination rarely produces turbid growth or obvious cell damage. Viable mycoplasma can be recovered from work surfaces seven days after inoculation, and mycoplasma can also pass through bacteria-retaining filters. At their maximum population phase there can be as many as $10^8$ mycoplasma/ml of supernatant, at a ratio of 5:1 with the host cells. If present, mycoplasma 'grow' to detectable concentrations in the culture medium, they are then also adsorbed onto the cell surface. It is a moot point as to whether mycoplasma enter and survive within mammalian cells in culture.

*Mycoplasma* are capable of altering almost every property of an in vitro culture. They will deplete culture nutrients, in particular arginine. Infected eukaryotic cells exhibit aberrant growth, changes in metabolism and morphology. Certain biological properties have been implicated as virulence determinants; these include secretion or introduction of mycoplasmal enzymes such as phospholipases, ATPases, hemolysins, proteases and nucleases into the host cell milieu.

A major problem with mycoplasma is that their contamination is often covert, and unlike bacterial detection, cannot be easily visualised. Their resistance to antibiotics and ability to pass through normal bacterial sterilisation filters means that they can evade typical precautions of cell culture technique. As a result of the negative impact of having these contaminations going undetected, it has become evident that continuous screening is essential for any cell culture laboratory.

There are a number of studies that have shown that at least 10%-15% of cells in culture may be contaminated with mycoplasma. (Rottem and Barile 1993, McGarrity and Kotani 1985). Most cell biologists recognise the need to perform routine testing for mycoplasma, however due to the cost and inaccuracies of the currently available tests, this has so far remained an unrealised ideal.

The only accurate method available for the detection of viable mycoplasma is culture of the micro-organisms. However, the difficulty associated with their in vitro culture has proved problematic due to the complex media required for their cultivation (Razin et al 1998). Culture has also been considered to be the most sensitive method, as it is said to be able to detect a single viable organism. However, the results take two to three weeks by highly skilled staff with very specific culture requirements. The time taken is a result of the need to culture the cells to a sufficient number whereby they form colonies, which can then be distinguished using a Dienes stain. *Mycoplasma* can be cultured on agar and in broth culture, with most mycoplasma producing microscopic colonies with a characteristic 'fried egg' appearance, growing embedded in the agar, although some colonies may not grow completely embedded. There are some strains that cannot be readily grown using standard agar or broth culture media. These strains require cell-assisted culture for their isolation and identification. The latter approach aids in the identification and detection of mycoplasma species that adsorb to host cell surfaces (Rottem and Barile 1993). However, due to the complicated nature of the culturing procedures, these tests are most commonly done by mycoplasma testing service laboratories.

One of the simpler means of detecting mycoplasma in samples is the assay of DNA using a fluorochrome. One of the most commonly used is 4',6-diamine-2-phenylindole dihydrochloride (DAPI), but Hoecsht staining is considered to be the method of choice. Cell culture samples are taken, fixed and stained with Hoechst 33258 (bisbenzamide) and examined under UV epifluorescence (Battaglia et al 1994, Raab 1999). If there are mycoplasma associated with the cells, then the cell nuclei will appear surrounded by fluorescing structures in the cytoplasm. Negative cells are represented by just the nuclear staining of the cellular DNA. Accurate interpretation of results from DNA staining requires an experienced eye, it also needs specialist equipment i.e. a fluorescence microscope. *Mycoplasma* detection by PCR is a commonly used test by external service laboratories, and is also performed in those laboratories that have the appropriate equipment. The primers used in mycoplasma PCR kits anneal to conserved regions of the mycoplasma genome, allowing the detection of several species (Raab 1999). Most commercially available PCR kits require that the amplified products be analysed by agarose gel electrophoresis, with the resulting banding patterns determining the contaminating species present. However visualisation of banding patterns is subjective.

The *Mycoplasma* PCR ELISA from Roche (Raab 1999) relies on a different system, and cannot distinguish between species. This kit includes digoxigenin-dUTP, and the PCR product is captured onto the surface of wells in a microtitre plate coated with anti-digoxigenin-peroxidase conjugate. The coloured product with tetramethylbenzidine (TMB) is visualised using a standard ELISA plate reader.

Life Technologies has developed the MYCOTECT™ Kit, based on the activity of adenosine phosphorylase, which is found only in small amounts (if at all) in mammalian cells (Verhoef et al 1983). This enzyme converts 6-methylpurine deoxiriboside (6-MPDR) into two toxic products (6-methylpurine and 6-methylpurine riboside). The assay requires addition of the contaminated cell line to an indicator cell line grown in a 24 well tissue culture plate. The 6-MPDR substrate is added and after 3-4 days of additional growth, a crystal violet stain is added to test for viability of the indicator cells, in that mycoplasma positivity results in production of these toxic agents. Although it has been reported to detect 1 mycoplasma cell per 200,000 target cell, if the medium conditions are adjusted to favour the growth of mycoplasma (Whitaker et al 1987), the main disadvantage of this system is that it is labour intensive and time consuming.

It is possible to detect mycoplasma antigens using immunoassays, employing antibodies raised against mycoplasma antigens. For example, the detection of *M. pneumoniae* in clinical samples (Daxboeck et al 2003) Use of different antibodies allows for species identification. There are a number of commercially available kits, for example IDEXX laboratories (US), supply enzyme linked immunosorbent assays (ELISA) for the detection of a number of mycoplasma that have implications in animal health.

Most of the known assays take a minimum of 24 hours to complete, need expensive equipment and a significant amount of expertise. Also, they are strain-specific assays. None are generic, that is, have the ability to detect mycoplasma species in general.

UK patent No. 2 357 336 B describes an assay which can be used to detect mycoplasmas in cell cultures. The assay is based on the observation that mycoplasmas over-produce the enzyme ATPase in large amounts. The ATPase activity of mycoplasmas converts sufficient cellular or externally added ATP to ADP, to make the ADP detectable. Hence, the assay is based on detection of ADP and this is carried out by adding to the sample an enzyme containing reagent (containing a combination of pyruvate kinase and phosphoenol pyruvate; adenylate kinase; glycerol kinase, myokinase; or a combination of creative kinase and creative phosphate), which converts the ADP to ATP and detecting ATP using a bioluminescent reaction.

The disclosure of UK patent No. 2,357,336 is incorporated herein, including for the purpose of possible amendment.

The present invention seeks to provide further means for detecting mycoplasmas in samples, such as samples from cell cultures.

According to a first aspect the invention provides a method of detecting the presence of contaminating mycoplasma in a test sample comprising:
 (i) providing a test sample;
 (ii) detecting and/or measuring the activity (B) of acetate kinase and/or carbamate kinase in the test sample, and said activity being indicative of the presence of contaminating mycoplasma; and
 (iii) identifying the test sample as contaminated with mycoplasma on the basis of detection and/or measurement of said activity in step (ii).

Preferably, the method further comprises the following steps performed after step (ii) but before step (iii):
 (iia) obtaining acetate kinase and/or carbamate kinase activity information (A) detected and/or measured in a corresponding control sample; and
 (iib) comparing the activity detected and/or measured in the test sample (B) with that in the control sample (A);
 wherein the test sample is identified as contaminated with mycoplasma in step (iii) if the activity (B) detected and/or measured in the test sample in step (ii) is greater than that of the control sample (A) in step (iia), that is, the ratio $$\frac{B}{A}$$

is greater than one.

In a second aspect the invention provides a method wherein detecting and/or measuring the activity (B) of acetate kinase and/or carbamate kinase in the test sample in step (ii) and/or obtaining acetate kinase and/or carbamate kinase activity information (A) in a corresponding control sample in step (iia) comprises detecting and/or measuring the appearance and/or disappearance of one or more of the substrates and/or one or more of the products of the following reactions:

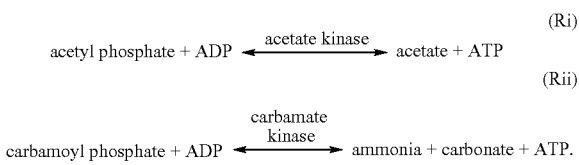

Preferably, the detecting and/or measuring step comprises detecting and/or measuring ATP. Still more preferably, the ATP is detected and/or measured by a light-emitting reaction, especially a bioluminescent reaction.

Light-emitting systems have been known and isolated from many luminescent organisms, including certain bacteria, protozoa, coelenterates, molluscs, fish, millipedes, flies, fungi, worms, crustaceans, and beetles, particularly the fireflies of the genera *Photinus, Photuris,* and *Luciola* and click beetles of genus *pyrophorus*. In many of these organisms, enzymatically catalyzed oxidoreductions take place in which the free energy change is utilised to excite a molecule to a high energy state. Then, when the excited molecule spontaneously returns to the ground state, visible light is emitted. This emitted light is called "bioluminescence".

Beetle luciferases, particularly that from the firefly species, *Photinus pyralis*, have served as paradigms for understanding of bioluminescence since the earliest studies. The *P. pyralis* luciferase is an enzyme which appears to have no prosthetic groups or tightly bound metal ions and has 550 amino acids and a molecular weight of about 60,000 daltons; the enzyme has been available to the art in crystalline form for many years. Studies of the molecular components in the mechanism of firefly luciferases in producing bioluminescence have shown that the substrate of the enzymes is firefly luciferin, a polyheterocyclic organic acid, D-(−)-2-(6'-hydroxy-2'-benzothiazolyl)-$^2$-thiazoline-4-carboxylic acid (herein-after referred to as "luciferin", unless otherwise indicated).

ATP can be detected using the following bioluminescent reaction.

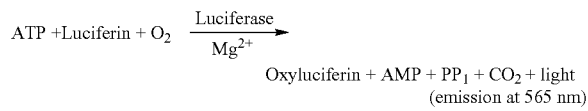

The emitted light intensity is linearly related to the ATP concentration and is measured using a luminometer.

Luciferase has been used as a means of assaying minute concentrations of ATP; as little as $10^{-16}$ molar ATP can be detected with high quality preparations of the enzyme. The luciferase-luciferin reaction is highly specific for ATP. For example, deoxy-ATP produces less than 2% of the light generated by ATP, and other nucleoside triphosphates produce less than 0.1%.

Crystalline luciferases can be isolated directly from the light organs of beetles. cDNAS encoding luciferases of several beetle species (including, among others, the luciferase of *P. pyralis* (firefly), the four luciferase isozymes of *P. plagiophthalamus* (click beetle), the luciferase of *L. cruciata* (firefly) and the luciferase of *L. lateralis*) (de Wet et al., 1987, Masuda et al., 1989, Wood et al., 1989, European Patent Application Publication No. 0 353 464) are available. Further, the cDNAs encoding luciferases of any other beetle species, which make luciferases, are readily obtainable by the skilled using known techniques (de Wet et al., 1986, Wood et al., 1989).

With the cDNA encoding a beetle luciferase in hand, it is entirely straightforward to prepare large amounts of the luciferase in highly pure form by isolation from bacteria (e.g. *E. coli*), yeast, mammalian cells in culture, or the like, which have been transformed to express the cDNA.

Further, the availability of cDNAs encoding beetle luciferases and the ability to rapidly screen for cDNAs that encode enzymes which catalyze the luciferase-luciferin reaction (see de Wet et al., 1986, supra, and Wood et al., supra) also allow the skilled person to prepare, and obtain in large amounts in pure form, mutant luciferases that retain activity in catalyzing production of bioluminescence through the luciferase-luciferin reaction.

Such a mutant luciferase will have an amino acid sequence that differs from the sequence of a naturally occurring beetle luciferase at one or more positions (White et al., 1996, WO 01/31028 and WO 00/24878). In the present disclosure, the term "luciferase" comprehends not only the luciferases that occur naturally in beetles but also the mutants, which retain activity in providing bioluminescence by catalyzing the luciferase-luciferin reaction, of such naturally occurring luciferases.

It is most preferred that in the method of the invention, after step (i) but before step (ii), the sample is treated so as to lyse any mycoplasma and thereby release their cellular contents into the sample. Skilled persons will understand that lysis can be effected by a variety of methods including application of chemicals, such as detergents and mechanical methods such as sonication etc.

Advantageously, the lysis is effected by treating the sample with a detergent, or other lysis method, which allows for the lysis of the *Mycoplasma* cell membrane but which does not affect the cell wall of any bacteria which may be present. Exemplary detergent treatment includes the use of low concentrations (e.g. 0.25% v/v) of a detergent, such as Triton X100.

The preferred lysis method is one that is sufficient to lyse the mycoplasmal membrane, but would be ineffective against bacterial cells. In studies comparing eukarytic cell lysis and bacterial lysis, it has been observed that non-ionic detergents (mainly polyethoxyethers) could be used to lyse somatic cells without affecting microbial cells (Schramm and Weyens-van Witzenberg 1989, Stanley 1989). It is the presence of the rigid cell wall that makes bacteria less sensitive to detergent lysis, and more rigorous lysis procedures are required to lyse bacterial cells. For efficient lysis and total protein release, bacteria often require exposure to enzymes such as lysozyme to breach the cell wall (Pellegrini et al 1992). The most preferred detergent mycoplasma lysis conditions are shown hereinafter.

However, a contamination with bacteria will produce turbid growth, and bacteria are also visible when viewing a cell culture under phase contrast microscopy. These bacterial cultures can be detected quite easily and discarded straight away.

Unlike bacteria, mycoplasma will pass through a 0.45 µM filter used for filter sterilisation (Baseman and Tully 1997), and it is possible to distinguish between a bacterial and mycoplasmal contamination through the addition of a filtration step.

Hence, in preferred embodiments of the invention the test sample is passed through a bacterial filter in step (i). Of course, skilled persons will appreciate that if the test sample is treated to remove bacteria, for example by passing it through a bacteria-retaining filter, it is not important to lyse mycoplasma selectively, i.e. without lysing bacteria.

In a preferred embodiment, ADP is added to the test sample prior to the detecting and/or measuring step (ii). However, the assay can also utilise endogenous ADP.

or both. In addition to those listed below there are a number of reptile, insect and plant infecting mycoplasmas where biochemical investigations have identified the use of these same pathways (Kirchoff et al 1997, Forsyth et al 1996, Taylor et al 1996 and Tully et al 1994).

TABLE 2

ATP generation by mycoplasma through glucose or arginine utilisation.

| Species | Preferential ATP Generation Pathway | Enzymes Utilised |
|---|---|---|
| M. hyorhinis | Glucose fermentation and Arginine lysis | Acetate kinase/Carbamate kinase |
| M. orale | Arginine lysis | Carbamate kinase |
| M. fermentans | Arginine lysis and glucose fermentation | Carbamate kinase/Acetate kinase |
| M. salivarum | Arginine lysis | Carbamate kinase |
| M. arginii | Arginine lysis | Carbamate |
| A. laidlawii | Glucose fermenting | Acetate kinase |
| U. urealyticum | Glucose fermenting | Acetate kinase |
| M. pneumoniae | Arginine lysis and glucose fermentation | Carbamate kinase/Acetate kinase |
| M. mycoides | Glucose fermenting | Acetate kinase |
| M. arthritidis | Arginine lysis | Carbamate kinase |
| Anaeroplasma sp | Arginine lysis | Carbamate kinase |
| M. hominis | Arginine lysis | Carbamate kinase |
| A. vituli | Glucose fermenting | Acetate kinase |
| M. lagogenitalium | Glucose fermenting | Acetate kinase |
| M. mycoides | Glucose fermenting | Acetate kinase |
| M. penetrans | Arginine lysis and glucose fermentation | Carbamate kinase/Acetate kinase |
| M. pirum | Arginine lysis and glucose fermentation | Carbamate kinase/Acetate kinase |
| M. incognitis | Arginine lysis and glucose fermentation | Carbamate kinase/Acetate kinase |

In a preferred embodiment, a mycoplasma substrate reagent is added to the test sample prior to the detecting and/or measuring step (ii), the mycoplasma substrate reagent comprising: acetyl phosphate or a precursor thereof and/or carbamoyl phosphate or a precursor thereof.

By "a precursor thereof" we include one or more compounds from which acetyl phosphate and/or carbamoyl phosphate can be generated. Exemplary reactions are outlined below:

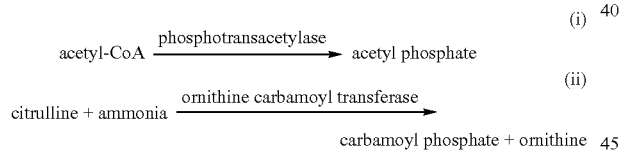

Hence, instead of adding acetyl phosphate to the mycoplasma substrate reagent, one could include a precursor, such as acetyl-CoA.

Similarly, instead of carbamoyl phosphate one could add a precursor, such as citrulline and ammonia to the mycoplasma substrate reagent.

It is most preferred that both acetyl phosphate and carbamoyl phosphate and/or precursors thereof are added to the sample prior to step (ii), in the methods of the invention. This enables a generic assay for mycoplasma contamination to be carried out because mycoplasmas utilise either or both substrates by means of their acetate kinase and/or carbamate kinase enzymes.

Alternatively, a more specific assay can be produced by only using one of the above substrates or precursors thereof. Such an assay will be specific for mycoplasma which only use one of the enzymes acetate kinase or carbamate kinase. The following table 2 cites some examples of the members of the Mollicutes family (parasitise mammalian hosts) that utilise acetate kinase preferentially, carbamate kinase preferentially, Most preferably, in all of the methods of all aspects of the invention, the "corresponding control sample" is the test sample prior to a mycoplasma lysis treatment and/or addition of a mycoplasma substrate and/or a time interval (e.g. more than approximately 30 minutes). In this preferred embodiment both of the activity measurements are carried out on the same sample, the test sample. A first activity measurement (A) is taken either before or concurrent with a mycoplasma lysis step then, after addition of a mycoplasma substrate and/or a time interval (e.g. more than approximately 30 minutes), a second activity measurement (B) is taken. If the value of $$\frac{B}{A}$$

is greater than one the test sample is identified as contaminated with mycoplasma.

Skilled persons will appreciate that the "corresponding control sample" could also be a predetermined negative control sample, but this is less preferred.

In an embodiment, the control sample has been shown to be free from mycoplasma contamination. Suitable methods for doing this include PCR testing, DNA fluorescent staining or culture methods as described herein.

Thus, in one embodiment, by "corresponding control sample" we mean a sample which contains substantially the same material as that contained in the test sample, but which, unlike the test sample, has been shown to be free from mycoplasma contamination. Skilled persons will appreciate that a mycoplasma uncontaminated condition can be shown by a variety of known methods. A number of suitable methods are reviewed by Rottem and Barile 1993, while an outline of testing kits and services is given in Raab et al 1999.

The test sample and/or control sample can be a cell sample, such as a cell culture sample, especially a culture of mammalian cells. Some examples are listed in the following table 3.

TABLE 3

Commonly cultured cell lines that have been tested using the assay method.

| Cell Name | Cell type | Supplier/Deposit Number |
|---|---|---|
| K562 | Human Chronic Myelogenous Leukaemia | ECACC 89121407 |
| U937 | Human Histiocytic Lymphoma | ECACC 87010802 |
| HL-60 | Human Promyelocytic | ECACC 88112501 |
| Cem-7 | Human Acute T-Lymphoblastic Leukaemia | ATCC CCL-119 |
| Jurkat | Human T-Cell Leukaemia | ECACC 88042803 |
| CHO | Chinese Hamster Ovary | ECACC 85050302 |
| COS-7 | Simian Kidney Cells, SV40 transformed | ECACC 87021302 |

TABLE 3-continued

Commonly cultured cell lines that have been tested using the assay method.

| Cell Name | Cell type | Supplier/Deposit Number |
|---|---|---|
| Vero | African Green Monkey Kidney Cells | ECACC 84113001 |
| MRC5 | Human Foetal Lung | ECACC 84101801 |
| HUVEC | Human Umbilical Vein Endothelial Cells | ECACC 89110702 |
| BSMC | Human Broncial Smooth Muscle Cells | Cambrex CC-2576 |
| NHEK | Normal Human Epidermal Keratinocytes | Cambrex CC-2503 |
| MCF-7 | Human Breast Adenocarcinoma | ECACC 86012803 |
| AoSMC | Aortic Smooth Muscle Cells | Cambrex CC-2571 |
| A549 | Human Lung Carcinoma Cells | ECACC 86012804 |
| HepG2 | Human Hepatocyte Carcinoma | ECACC 85011430 |
| FM3A | Mouse Mammary Carcinoma | ECACC 87100804 |
| PC12 | Rat Adrenal Pheochromocytoma | ECACC 88022401 |
| ARPE-19 | Human Retinal Pigment Epithelial Cells | ATCC CRL-2302 |
| RT112 | Human Bladder Carcinoma | ECACC 85061106 |

Where ECACC represents the European Collection of Animal Cell Culture, ATCC represents the American Tissue Culture Collection, and Cambrex represents Cambrex Bio Science Wokingham, UK Also, it would be possible to test mammalian primary cell types, plus all those cells held by tissue banks, for example the ATCC and ECACC.

It is notable that the assays of the invention can be utilised to detect mycoplasma contamination in cultures of both adherent cells (e.g. HepG2, A549, CHO and COS cells) and cells which culture in suspension (e.g. Jurkats, U937, K562 and HL-60 Cells.)

Preferably the sample to be tested is from the cell culture supernatant which has previously been centrifuged to remove cellular material. However, it is also possible to perform the assay in the presence of cells or cellular debris.

Cell-free samples can also be tested using the methods of the invention. For example, the methods of the invention are particularly useful for testing samples of cell-free reagents, such as tissue culture media, and typically those containing animal-derived materials, such as serum (e.g. foetal calf serum), trypsin, and other culture supplements, etc. Examples of some commonly used media and supplements that may be tested in this manner are shown in table 4.

TABLE 4

Tissue culture media and supplements that may be tested using the assay system.

| Culture Media | Sera | Growth Factors | Other Tissue Culture Reagents |
|---|---|---|---|
| RPMI | Foetal Calf | Epidermal growth factor | Trypsin |
| DMEM | Newborn Calf | Transforming growth factor | Insulin |
| Eagle's MEM | Horse | Granulocyte-colony stimulating factor | Transferrin |
| Glasgow MEM | Human | Granulocyte-macrophage CSF | Collagen |
| Ham's F12 | Porcine | Nerve growth factor | Fibronectin |
| IMDM | Chicken | | Vitronectin |
| Medium 199 | Rabbit | | Amino acid supplemnts |
| McCoy's 5A | Sheep | | Gelatin |
| Hybridoma | | | Albumins |
| CHO media | | | Pancreatin |
| Embryo Culture Media | | | Bovine pituitary extract |
| Williams Medium E | | | |

A third aspect of the invention provides a method of detecting the presence of mycoplasma in a test sample, comprising the following steps:

(i) providing a test sample;
(ii) without adding an exogenous reagent (e.g. substrates for kinase activity) to convert ADP to ATP, detecting or measuring ATP in the test sample using a bioluminescent reaction to obtain an ATP and/or light output measurement (A);
(iii) obtaining an ATP and/or light output measurement (B) from a corresponding control sample;
(iv) comparing the ATP and/or light output measurement ratio $$\frac{B}{A};$$

and
(v) identifying the test sample as contaminated with mycoplasma in the event that the ratio $$\frac{B}{A}$$

is greater than one.

As mentioned in connection with the earlier aspects of the invention, it is most preferred that *Mycoplasma* lysis treatment and/or addition of mycoplasma substrate and/or a time interval occurs before step (ii).

As mentioned in connection with the earlier aspects of the invention, it is most preferred that the "corresponding control sample" is the test sample except that it has not been subjected to *Mycoplasma* lysis treatment and/or addition of mycoplasma substrate and/or left for a time interval (e.g. more than approximately 30 minutes).

In other words, both measurements are taken from the test sample. Thus, in a preferred embodiment, the control ATP and/or light output measurement is taken following addition to the sample of the mycoplasma detection reagent containing the detergent and luciferase/luciferin plus AMP, and the test ATP and/or light output measurement is taken following addition of substrates for kinase activity (or precursors thereof).

A fourth aspect of the invention provides an in vitro process for treating a cell culture to remove mycoplasma contamination comprising:—treating a mycoplasma contaminated cell culture with an agent to remove or destroy mycoplasma; and subsequently testing a sample from the culture for mycoplasma contamination using a method of the invention; if necessary, repeating the process one or more times until mycoplasma contamination is not detected in the sample.

Most routine antibiotics used in cell culture are ineffective against mycoplasma. There are some agents that show inhibitory activity, these include gentamicin sulfate, kanamycin sulfate and tylosin tartrate (www.unc.edu/depts/tcf/mycoplasma.htm). There are a number of commercial treatment products, including *Mycoplasma* Removal Agent (ICN-Flow), a derivative of the quinolone family of antibiotics, also a non-antibiotic treatment from Minerva Biolabs (Berlin, Germany), Mynox®. The US company Invivogen supply Plasmocin™, which has two bactericidal components, one that acts on protein synthesis and the other that inhibits DNA replication. The antibiotics tetracycline and ciprofloxacin are reported to have success rates of less than 80-85% (www.unc.edu/depts/tcf/mycoplasma.htm). It is therefore extremely difficult to completely irradicate mycoplasma from cultures, once a contamination has taken hold.

Most of the effective antibiotics are quinolone derivatives, and the effectiveness of different antibiotics varies according to the mycoplasma species being tested. Duffy et al 2000, investigated *M. pneumoniae, M. hominis, M. fermentans, M. genitalium* and *U. urealyticum* viability against the quinolone gemifloxacin, and compared with a number of antibiotics including tetracycline, clindamycin and other quinolones. The results showed variable responses between species, however gemifloxacin performed better than tetracycline. There are some species that show resistance to tetracyclines, due to acquisition of the tetM gene. This is a frequent occurrence, and is complicated by variations in the responses of species dependent upon the source of mycoplasma. For example, mycoplasma exposed to antibiotics in eukaryotic cell culture have different profiles from the same species isolated from a human or animal source (Taylor-Robinson and Bebear 1997). While the reported success of anti-mycoplasma treatments appears highly variable, a recent study by Uphoff et al 2002, reports that 96% of leukaemia-lymphoma cell lines were rendered free of mycoplasma with at least one of the treatments tested.

Examples which embody various aspects of the invention will now be described with reference to the accompanying figures in which:—

FIG. 1: The kinetics of ATP generation in the presence of *M. hyorhinis* contamination.

Figure 2:
Figure 2:
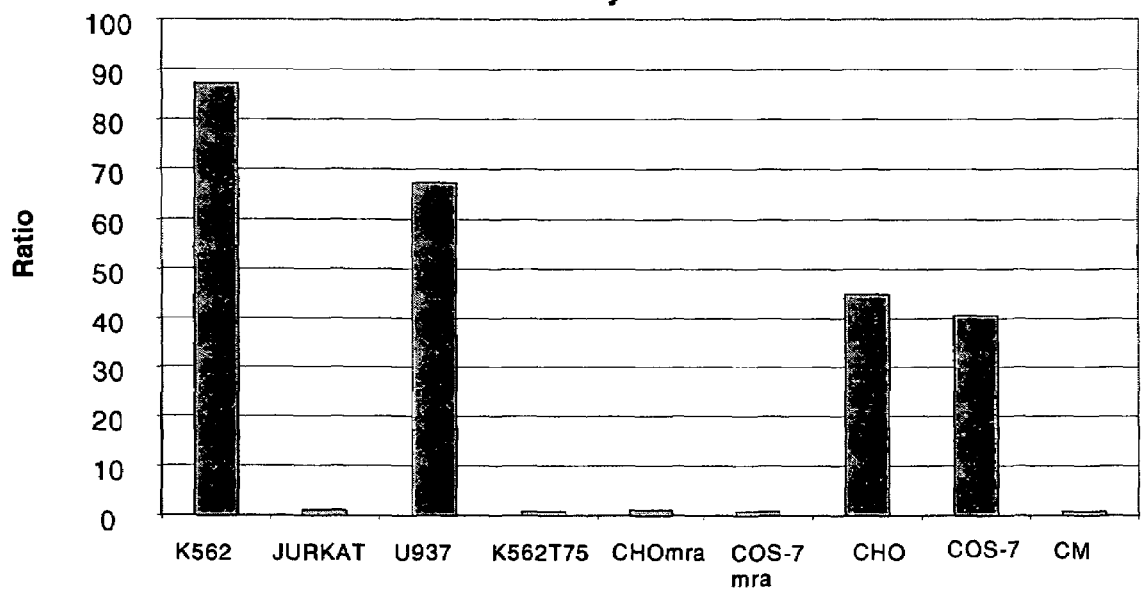

FIG. 2: A Comparison between the PCR kit from Stratagene and a preferred embodiment of the invention ratios.

Figure 3:
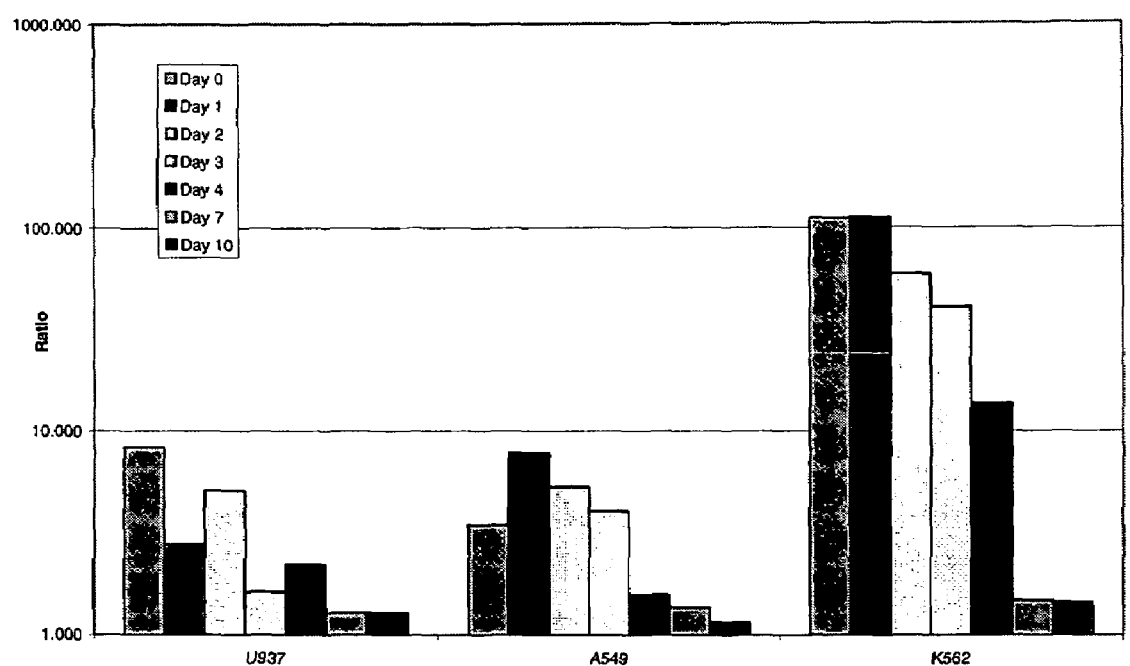

FIG. 3: Treatment of contaminated cell lines with *Mycoplasma* Removal Agent according to a preferred embodiment of the invention.

Figure 4:
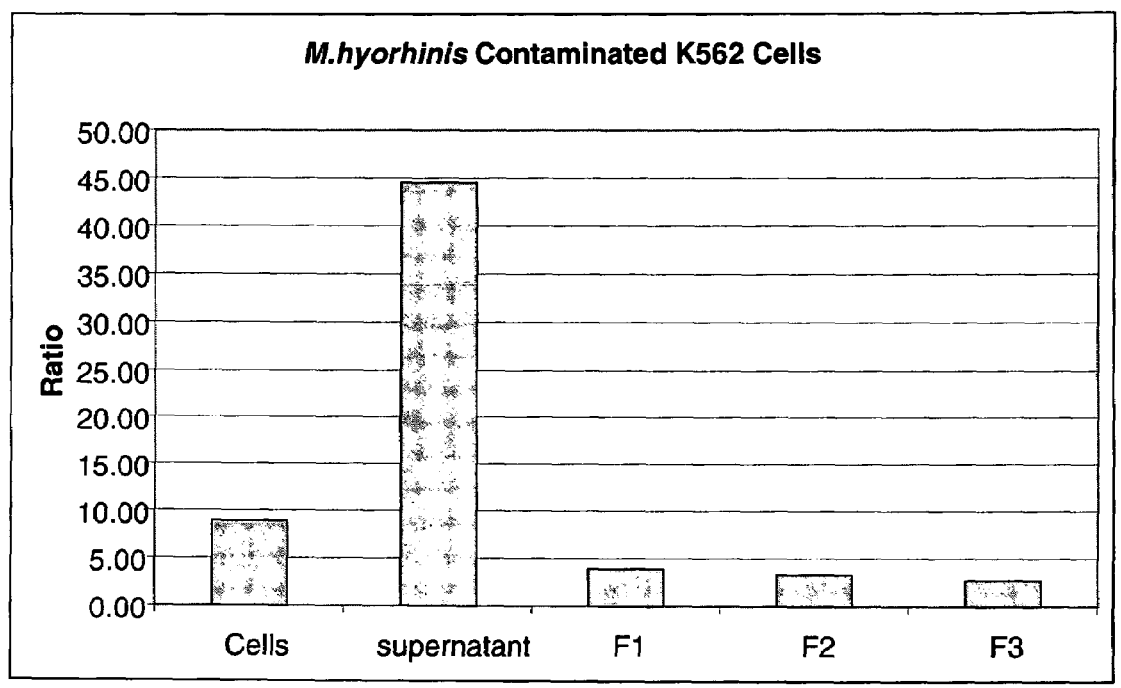

FIG. 4: Ratio data with cells, supernatants and supernatants filtered through a 0.45 µm (F1), 0.22 µm (F2) and 0.1 µm (F3) filters.

Figure 5:
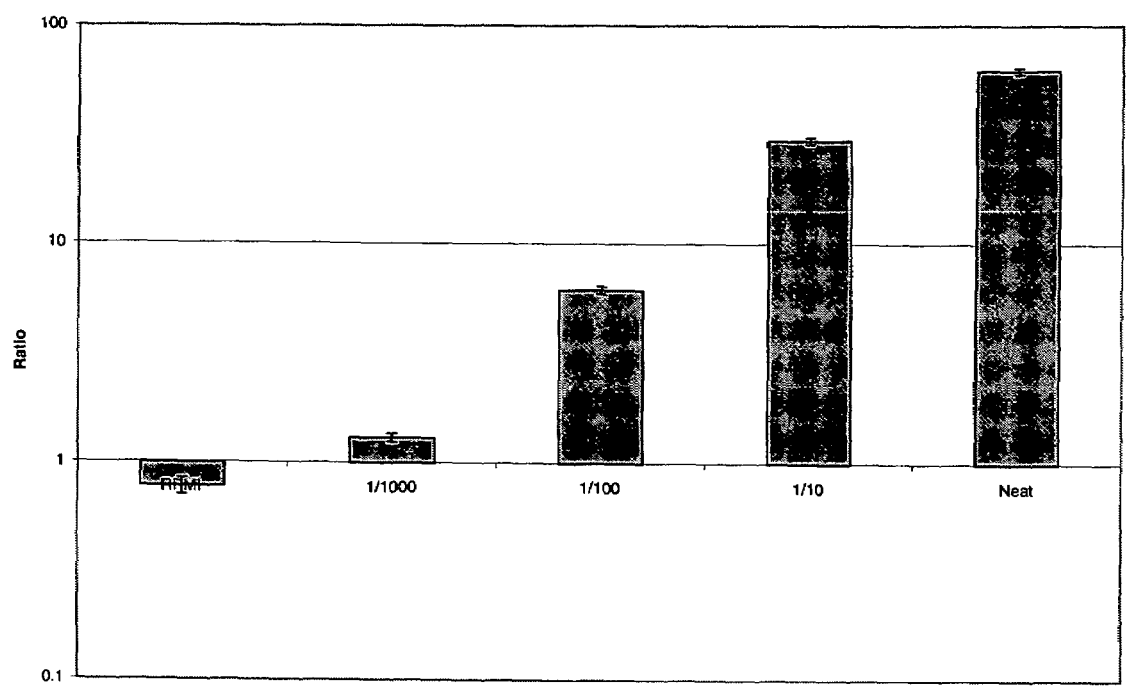

FIG. 5: Effect of supernatant dilution.

Figure 6:
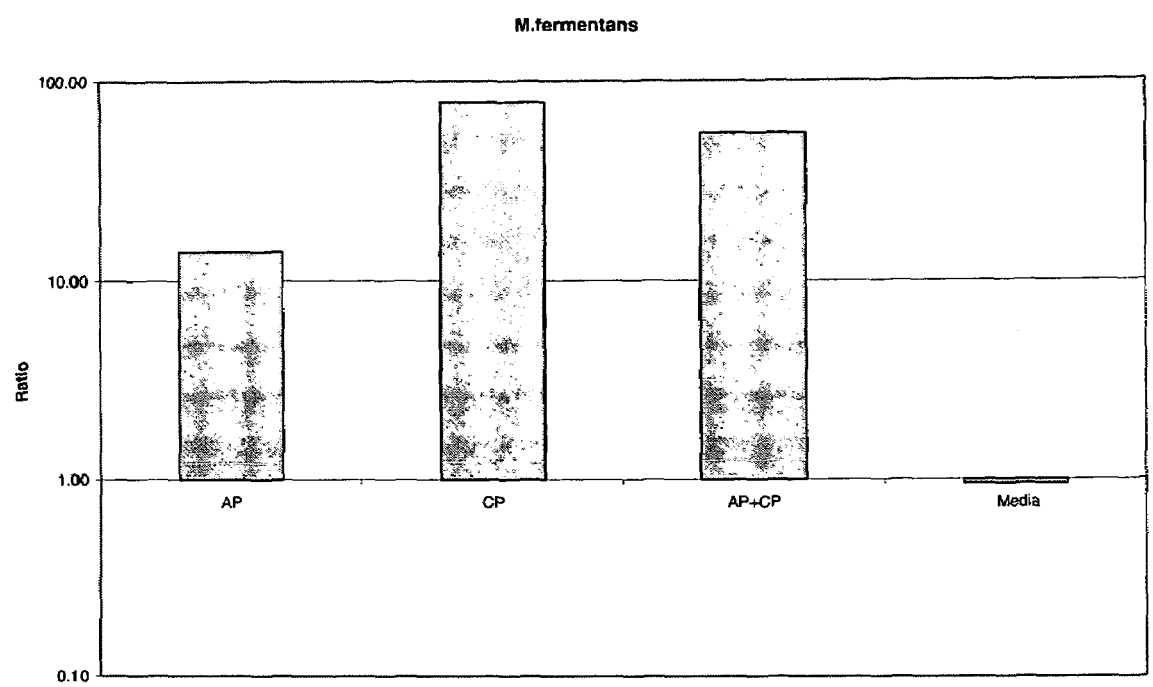

FIG. 6: *M. fermentans* at 7900 CFUs/well, tested against the different substrates.

Figure 7:
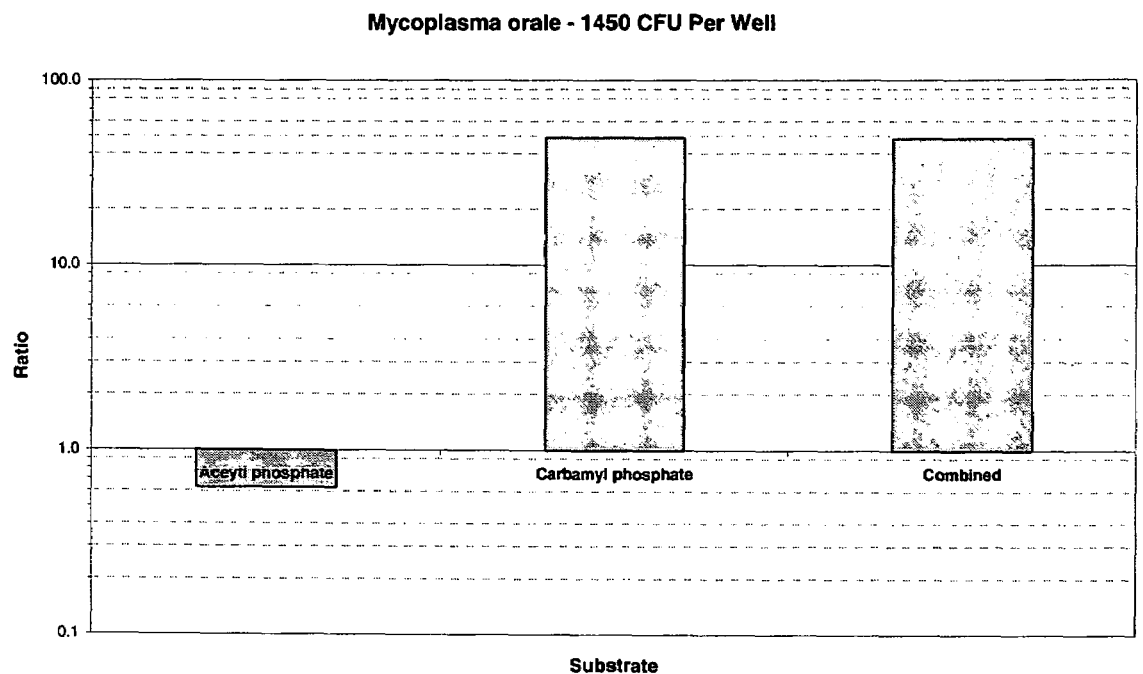

FIG. 7: *M. orale* stock at 1450 CFUs/well, tested against the different substrates.

Figure 8:
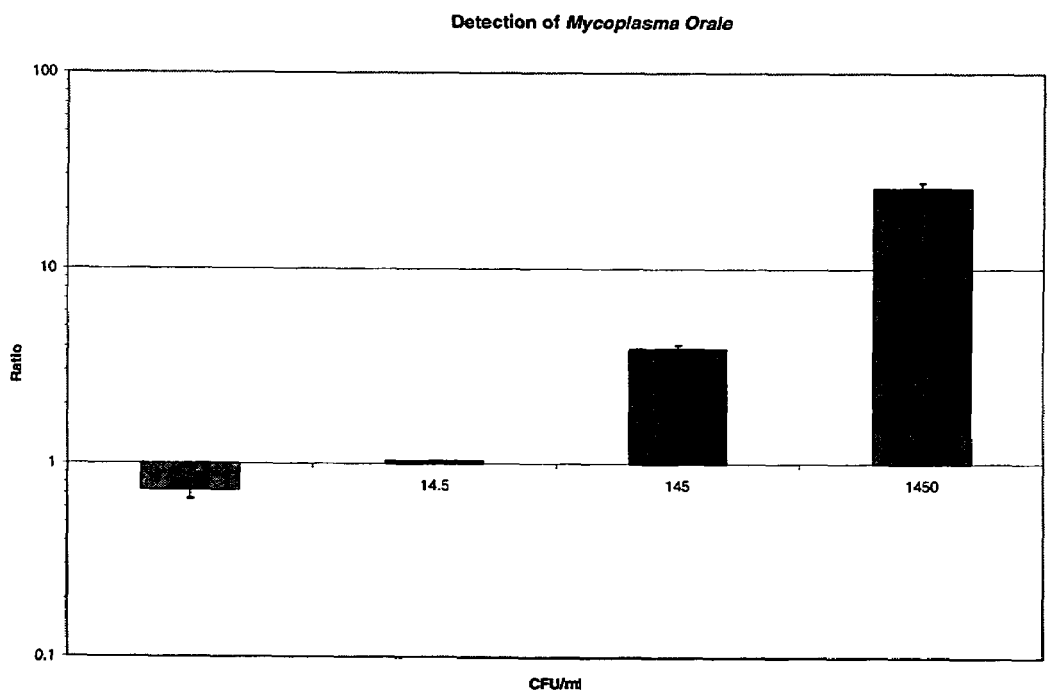

FIG. 8: Dilution of the *M. orale* stock to show sensitivity of the assay.

Figure 9:
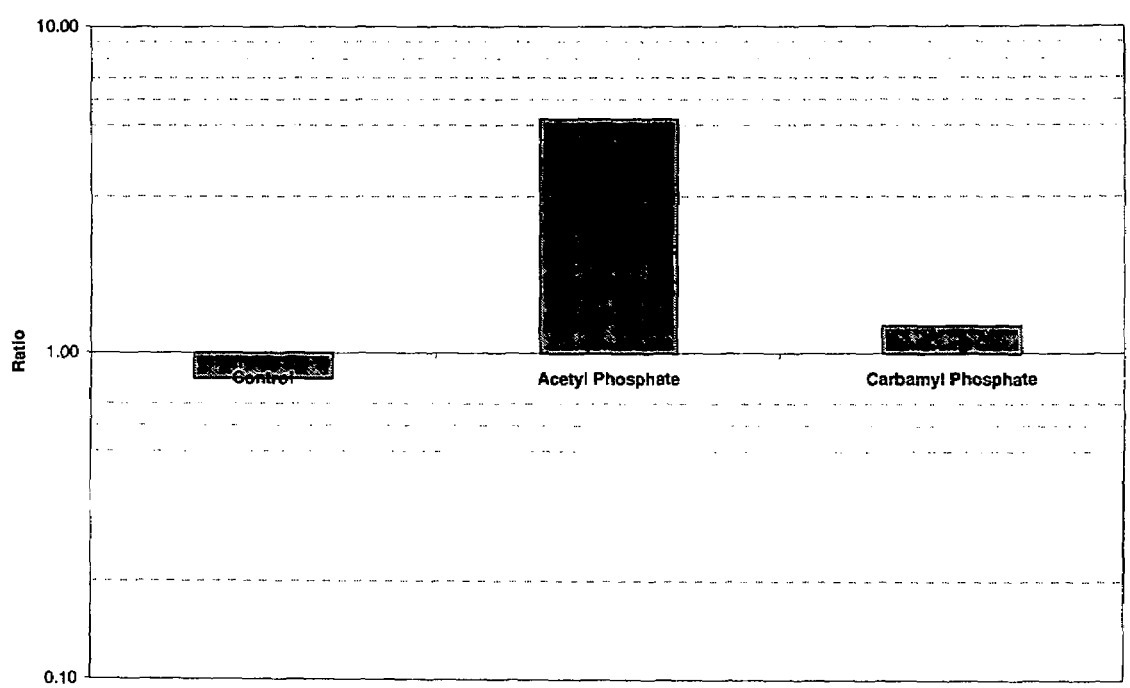

FIG. 9: *M. hyorhinis*, comparison of different substrate reagents.

Figure 10:
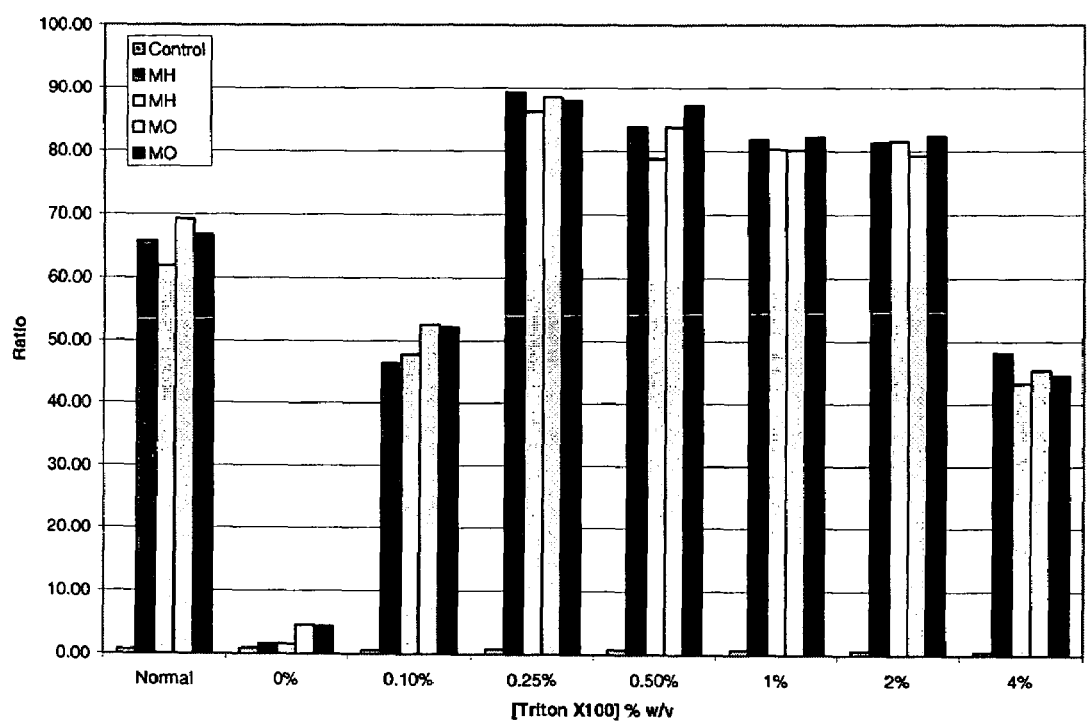

FIG. 10: The effect of Triton-X100 concentrations on the detection of mycoplasma enzyme activities in K562 cells infected with *M. hyorhinis* (MH) and *M. orale* (MO).

Figure 11:
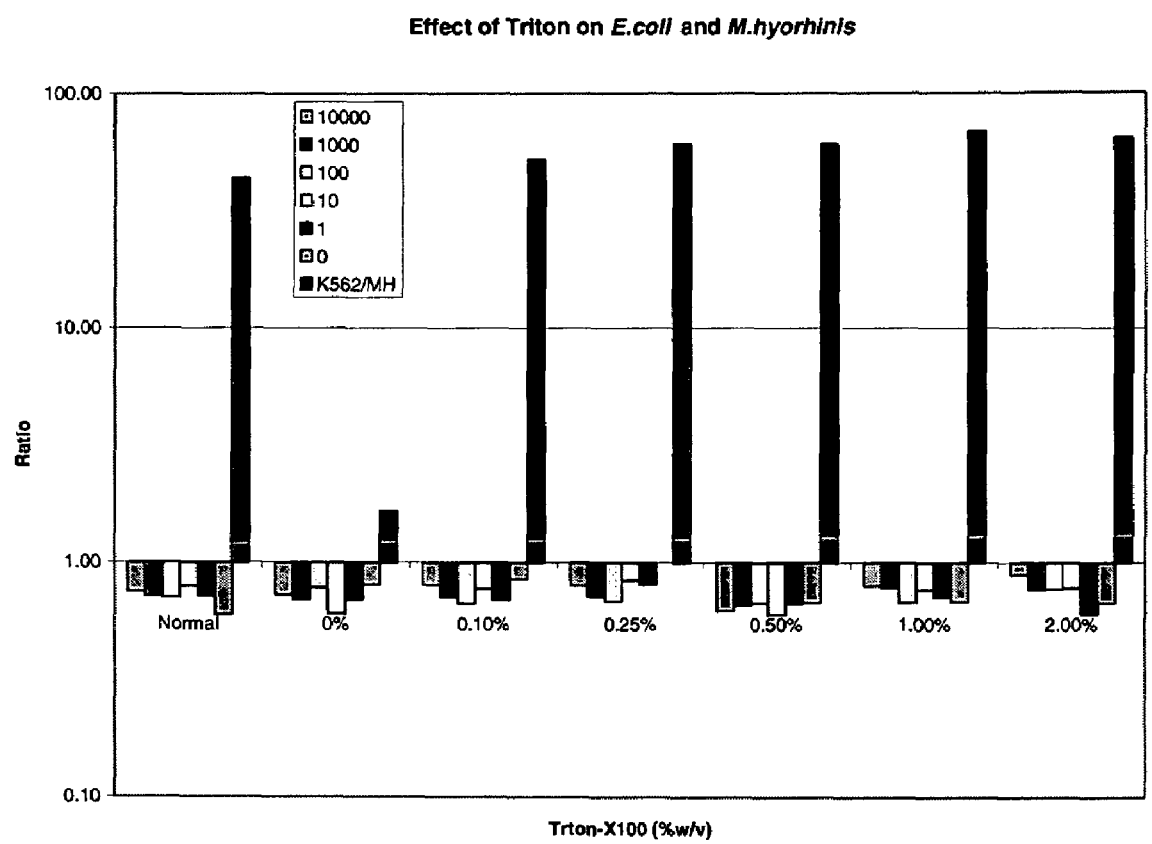

FIG. 11: Shows the effect of increasing Triton-X100 concentrations on K562 cells contaminated with *M. hyorhinis* (MH) compared to increasing numbers (1-10,000 cells/100 µl sample) of bacterial cells (*E. coli*).

EXAMPLE 1

Assay Method of the Invention

The principle of the preferred assay method is to supply the appropriate substrates for mycoplasmal enzymes. If mycoplasma contamination is present, there is a conversion of ADP to ATP which can then be measured, preferably by the luciferase-luciferin reaction.

Mycoplasma Detection Reagent is added and, after approximately 5 minutes, an initial light output reading (A) is taken, the *Mycoplasma* Substrate (MS) is added and any enzymatic activity is allowed to progress for approximately 10 minutes, at which point a second light reading (B) is taken.

If there is mycoplasmal contamination then the second reading (B) will be higher when compared to the first reading (A), giving a ratio B/A of greater than 1. If the culture is negative (uncontaminated by mycoplasma), then the ratio B/A will be 1 or most often less than one due to the luminescent light signal decay usually seen over time. FIG. 1 demonstrates the kinetics of the reaction. Typically, the ratio $$\frac{B}{A}$$

seen with mycoplasma contamination is much greater than 1, for example FIG. 1 shows a ratio of 114.

A preferred assay kit of the invention comprises a *Mycoplasma* Detection Reagent (MDR); *Mycoplasma* Assay Buffer (MAB) for reconstitution of MDR and the *Mycoplasma* Substrate (MS). MDR and MS are preferably provided as lyophilised preparations.

All mycoplasma generate ATP through either the acetate kinase pathway or the carbamate kinase pathway. The *Mycoplasma* Substrate of the invention contains substrates for one or both of these enzymatic reactions. ADP is a requirement for both enzymes, and is preferably supplied in excess in the *Mycoplasma* Detection Reagent of the invention to drive the generation of ATP formation.

The MDR is added to a sample of culture supernatant that has previously been centrifuged to remove cellular material, although it is possible to perform the assay in the presence of cells. Alternatively or additionally, the test sample can be passed through a bacterial filter.

The MDR contains substrates for luciferase, luciferin and other co-factors plus AMP and ADP. The *Mycoplasma* Substrate (MS) contains carbamoyl phosphate and/or acetyl phosphate or precursors thereof, required for detection of the carbamate and/or acetate kinase activities.

A preferred sample volume is 100 μl to which 100 μl of reconstituted MDR is added. After approximately 5 minutes the first luminometric reading (A) is taken, this gives the base reading upon which the further ratio calculations $$\frac{B}{A}$$

are determined.

The assay methods of the invention have been used to investigate contamination by *Acholeplasma laidlawii*, *M. hyorhinis*, *M. fermentans*, *M. orale*, and *M. genitalium* and to detect a number of unknown mycoplasma contaminations.

The inventors have compared their data to detection of mycoplasma by PCR, and have shown that there is a correlation between ratios greater than one and detection of mycoplasmal DNA. This is shown in FIG. 2 where the positive PCR bands on the gel correlate with ratios of more than one.

EXAMPLE 2

Use of the Methods of the Invention in a Process for Removing *Mycoplasma* Contamination from a Cell Culture The inventors have also shown that we can detect a reduction in ratios $$\frac{B}{A}$$

as cells are treated with an exemplary *Mycoplasma* Removal Agent (ICN-Flow), a derivative of the quinolone family of antibiotics.

The manufacturers (ICN-Flow) recommend treatment for 7 days of cells in quarantine to ensure complete removal of contaminating mycoplasma.

However, the ratio data obtained using the assay methods of the invention showed that 7 days was not sufficient. This was evident from the fact that the ratios remained greater than one. Also after removal of treatment, and continued culture the ratios increased, and the cultures were again positive after PCR testing (Stratagene kit). These data are shown in FIG. 3, where three different cell lines were found to be contaminated with *M. hyorhinis*.

While the K562 and U937 cells are suspension cell lines, the A549 cells are an adherent cell type; these data therefore confirms that the assay can be used on both adherent and suspension cell types. This is also shown in FIG. 2 where the CHO and COS-7 cells are adherent cell types commonly used in cell culture laboratories.

FIG. 3 also shows that the treatment with MRA for 10 days with COS-7 and CHO cell cultures was sufficient to remove the contaminating mycoplasma.

EXAMPLE 3

Failure of Bacterial Filters to Exclude *Mycoplasma*

The inventors have also shown that culture supernatants put through a number of bacterial retarding filters continued to show positive ratios which is indicative of the presence of viable mycoplasma. This is shown in FIG. 4.

*Mycoplasma* can form colonies as large as 600 μm in diameter, but can also exist in their life cycle as single cells as small as 0.15 μm. Due to their small size mycoplasma can pass through the 0.45 μm and 0.22 μm filters commonly used to "sterilise" tissue culture reagents. FIG. 4 also confirms that the assay can be performed in the presence of cells, but that there is a reduced sensitivity of detection. Hence, it is preferred that the assay methods of the invention are performed on samples which are substantially cell free. This can easily be achieved by centrifugation of cell cultures and sampling of the supernatant and, optionally, filtration through a bacterial filter.

EXAMPLE 4

Sensitivity of Preferred Assays

As shown in FIGS. 5 and 8, dilution of the supernatants shows the sensitivity of the assays, in that a 1:1000 dilution of contaminated culture supernatant can still give ratios greater than 1. Dependent on the specific activity of the acetate kinase and carbamate enzymes in different mycoplasma (Mollicutes) species, it is possible to dilute samples out further. The dilution range will also vary according to the number of colony forming units in the test sample.

EXAMPLE 5

Variations of the Assay Methods of the Invention

The assay methods of the invention will work without the external exogenous addition of carbamate and acetate kinase substrates in the form of ADP, carbamoyl phosphate and acetyl phosphate or precursors thereof. In a contaminated culture sample the acetyl and carbamoyl phosphates or precursors thereof will be present endogenously together with sufficient cellular ADP, derived from the cell culture, to prime the reaction towards the formation of ATP. Alternatively, ADP can be generated by other externally added or cellular enzymes i.e. adenylate kinase utilising ATP and AMP.

It is possible to avoid direct addition of these substrates and have the system generate them itself. The use of acetate and ammonia along with ATP will cause the acetate kinase and carbamate kinase enzymes to generate acetyl phosphate and carbamoyl phosphate that can then be used by the same enzymes to generate ATP from ADP:

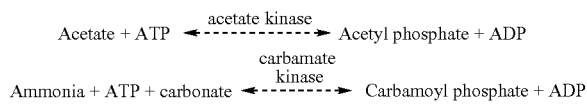

The two substrates could also be generated from "precursors" by utilising earlier parts of the glucose fermentation and argenine lysis pathways for example by the addition of acetyl- CoA and citrulline that could be used by mycoplasmal enzymes to synthesise acetyl phosphate and carbamoyl phosphate respectively.

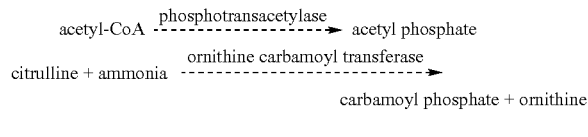

The following figures show the differences between the biochemical activities of *M. fermentans*, which generates ATP preferentially through the carbamate kinase pathway, but will also utilise the acetate kinase pathway. FIG. 6 shows the effect of adding the substrates for the enzyme pathways individually, and then in a combined reagent.

While *M. fermentans* utilises both pathways, *M. orale* utilises only the carbamate kinase pathway, and as shown in FIG. 7, positive ratios are only observed in the single carbamate reagent or the combined reagent. FIG. 8 shows the detection limits are as low as 14 CFU/well with *M. orale*.

The inventors have investigated a mycoplasma that preferentially utilises the acetate kinase pathway, namely *M. hyorhinis*. The data are shown in FIG. 9.

The inventors have tested over 15 different cell lines (see table 3) and shown that none of the cells have sufficient background enzymatic activity to impact upon the ratios and give false positives. The inventors, without wishing to be bound by theory, think the reason for this is that the pathways are anaerobic, and all mammalian cell cultures will generate ATP through oxidative phosphorylation. Hence, by using only carbamoyl phosphate or a precursor thereof or only acetyl phosphate or a precursor thereof, one can produce an assay method of the invention which will allow one to determine whether the mycoplasmal contaminants in question are from a group which uses the acetate kinase pathway, the carbamate kinase pathway, or both. This may have useful diagnostic applications.

The only bacteria that have acetate kinase activity are not those that are commonly found as contaminants of cell culture, with the possible exception of certain *E. coli* species that are handled in laboratories, principally for molecular biology purposes. However, activity with this organism, is only seen at very high inoculum concentrations where there is turbid growth and the resulting turbidity of the sample is readily observed by eye. Hence, the methods of the invention can be varied to include an initial screening step for bacterial contamination, if necessary. This can be achieved by a variety of methods, but is preferably carried out by passing the sample through a standard bacterial filter (Baseman and Tully, 1997).

EXAMPLE 6

Preferred Reagent Components for Use in the *Mycoplasma* Assay Methods and Kits of the Invention 1. *Mycoplasma* Detection Reagent (MDR) per 100 ml

| | |
|---|---|
| Magnesium acetate | 214.5 mg (10 mM) |
| Inorganic pyrophosphate | 178.4 µg (4 µM) |
| Bovine serum albumin | 160 mg (0.16%) |
| D-Luciferin | 10 mg (360 µM) |
| L-Luciferin | 250 µg (8.9 µM) |
| Luciferase (RY) | 85 µg |
| ADP | 250.5 µg (5 µM) |
| AMP | 69.44 mg (2 mM) |

* RY is the name given to the recombinant luciferase supplied by Lucigen. A mixture of D and L-Luciferin has been found to give a more stable light output than D-luciferin alone.

2. *Mycoplasma* Substrate (MS) per 100 ml

| | |
|---|---|
| Acetyl phosphate | 55.23 mg (3 mM) |
| Carbamoyl phosphate | 45.87 mg (3 mM) |

*Mycoplasma* Substrate (Ms) Precursors

Examples of reactions generating acetyl or carbamoyl phosphate:

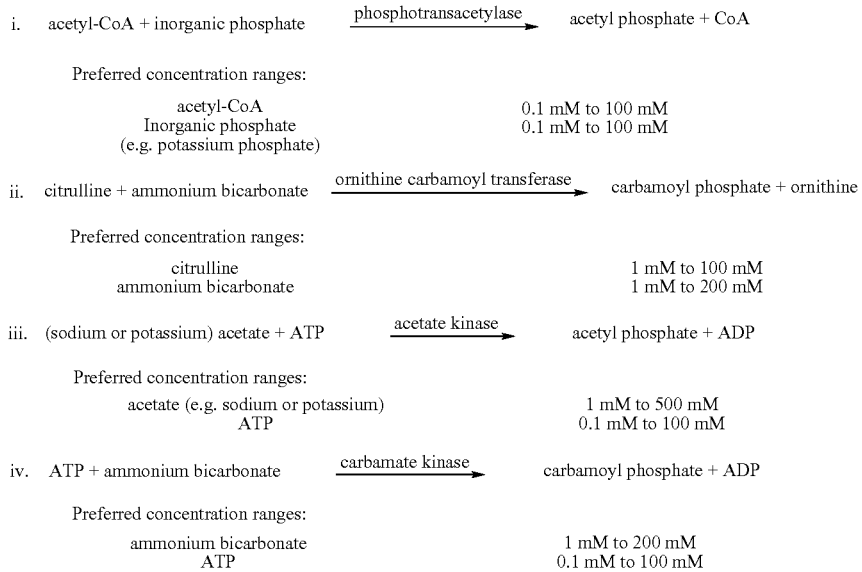

Suppliers
Sigma-Aldrich Company Ltd.
Fancy Road
Poole
Dorset
BH12 4QH
United Kingdom 3. *Mycoplasma* Assay Buffer (MAB) per 100 ml

| HEPES | 1.1915 g (50 mM) |
|---|---|
| EDTA | 74.44 mg (2 mM) |
| Triton X-100 | 250 µl (0.25%) |
| pH 7.50 | |

Preferred Concentration Ranges of Components for Use in the *Mycoplasma* Assay Methods and Kits of the Invention Preferred concentration ranges include ADP 1 µM to 100 mM, preferably 1 to 100 µM, more preferably 5 µM.

AMP 1 µM to 100 mM, preferably 0.1 mM to 10 mM, more preferably 2 mM.

Acetyl phosphate 1 µM to 100 mM, preferably 0.1 mM to 20 mM, more preferably 3 mM. Concentrations above 10 reduce the light output, but the assay still performs.

Carbamoyl phosphate 1 µM to 100 mM, preferably 0.1 mM to 20 mM, more preferably 3 mM.

EXAMPLE 7

Effects of Detergents on *Mycoplasma* Assay

Disruption of the viable mycoplasma cell membrane to allow for the release of the enzymes into the sample is a preferred embodiment of the assay method of the invention. This allows for binding of the substrates and generation of ATP. However, positive ratios indicating mycoplasma contamination can be obtained in the absence of any lysis treatment. The implication is that these enzymes can be released by viable mycoplasma The other possibility is that some non-viable organisms have released their contents through natural lysis.

The addition of even low concentrations of the non-ionic detergent Triton-X100, greatly increases the sensitivity of the assay by ensuring maximal release of the carbamate and acetate kinases into the sample.

The aim of the following experiments was to determine the concentrations of Triton-X100 in the Hepes-EDTA buffer on the ratios seen with mycoplasma contaminated K562 cell cultures. Two organisms were investigated, *M. hyorhinis* and *M. orale*.

FIG. 10 shows that it is possible to detect mycoplasmal enzymes in the absence of a detergent lysis step. It also shows a drop in the light output with concentrations greater than 4-5%, this is due to adverse effects of the detergent on the luciferase enzyme/reaction. However, it is still possible to detect positive activity with concentrations as high as 20% (v/v).

The inventors have also shown that the concentrations of Triton-X100 used in the above experiments did not result in any detectable carbamate or acetate kinase activity from the *E. coli* strain JM109 cells.

The above results confirm that there are no positive ratios with the bacterial cell number used. Increasing the Triton-X100 concentration to levels that have been reported to lyse bacterial cells (1-2%), still did not result in positive ratios above 1.

Generally biological detergents are commonly used to disrupt the bipolar membranes of lipids in order to release and then solubilise membrane bound proteins. Non-ionic detergents are non-denaturing and permit the solubilization of membranes without interfering with biological activity.

They have principally been used for the study of protein conformations and for the separation of hydrophilic proteins from membrane spanning hydrophobic proteins. Anionic and cationic detergents result in greater modification of protein structure and are more effective at disrupting protein aggregation. Zwitterionic detergents are also low-denaturing, but are effective at disruption of protein aggregates.

These different groups of detergents have been studied with a number of different cells types to efficiently lyse, and release and preserve the protein content, of both eukaryotic and prokaryotic organisms.

For the preferred Assays of the invention the required lysis agent is one that causes disruption of the mycoplasmal membrane and allows release of the metabolic enzymes that are required to react with the substrates. As there is no detergent removal or neutralisation step, it is therefore important that the chosen system does not interfere with the activity of the carbamate and/or acetate kinase, or the luciferase/luciferin/ATP reaction. It is also preferable to use a system that selectively causes the lysis of mycoplasma, with little or no effect on bacteria that may be potential contaminates of the cell cultures/samples.

The presence of a filtration step through 0.45 µm filters, however, should remove any contaminating larger microorganisms.

The key difference between bacteria and mycoplasma is the lack of cell wall, and it is the bacterial cell wall that makes bacteria more difficult to lyse. There are a number of fairly brutal methods that can bring about total lysis, these include pressure (French Press) and sonication. Other enzyme digest methods include lysozyme followed by the addition of detergents.

However, mycoplasma can be lysed with concentrations of Triton X-100 at around 1-2%.

Low concentrations of other non-ionic detergents, such as Brij®35 (0.4%) (Sigma-Aldrich Company Ltd.) and B-PER (1%) (Perbio Science UK Ltd.), do not have adverse effects on the luciferase enzyme, and are capable of disrupting the mycoplasmal membrane, without adversely affecting the luciferase reaction. The concentrations of these detergents can be taken up to 10% without loss of sensitivity of mycoplasmal detection.

Contaminating mycoplasma can be detected in the absence of a lysis step to disrupt the mycoplasmal membrane. However, addition of a gentle lysis step (0.25% Triton X-100 in Hepes-EDTA buffer) increases the sensitivity of the assay by releasing the mycoplasmal enzymes of interest into the reaction mixture.

The lysis step would preferably cause selective lysis of mycoplasma, while having little or no effect on bacterial cells. Low concentrations of most non-ionic detergents should do this. However, a filtration step would physically remove any contaminating bacteria, and allow for the use of any detergent but preferably those that do not inhibit either the luciferase reaction or the activity of carbamate kinase and acetate kinase.

EXAMPLE 8

Preferred Kit Contents

LT07-118 (Sufficient for 10 tests)

1. LT27-217 *Mycoplasma* Detection Reagent, Lyophilised. 2×600 µl vials.

2. LT27-218 *Mycoplasma* Assay Buffer. 1×10 ml bottle.

3. LT27-221 *Mycoplasma* Substrate. Lyophilised. 2×600 μl vials.

LT07-218 (Sufficient for 25 tests)
1. LT27-217 *Mycoplasma* Detection Reagent. Lyophilised. 5×600 μl vials.
2. LT27-218 *Mycoplasma* Assay Buffer. 1×10 ml bottle.
3. LT27-221 *Mycoplasma* Substrate. Lyophilised. 5×600 μl vials.

LT07-318 (Sufficient for 100 tests)
1. LT27-216 *Mycoplasma* Detection Reagent. Lyophilised. 1×10 ml vial.
2. LT27-220 *Mycoplasma* Assay Buffer. 1×20 ml bottle.
3. LT27-224 *Mycoplasma* Substrate. Lyophilised. 1×10 ml vial.

Preferred Reagent Compositions for Kits and Methods of the Invention

1. *Mycoplasma* Detection Reagent (MDR) per 100 ml

| | |
|---|---|
| Magnesium acetate[1] | 214.5 mg (10 mM) |
| Inorganic pyrophosphate[1] | 178.4 μg (4 μM) |
| Bovine serum albumin[1] | 160 mg (0.16%) |
| D-Luciferin[2] | 10 mg (360 μM) |
| L-Luciferin[2] | 250 μg (8.9 μM) |
| Luciferase (RY)[3] | 85 μg |
| ADP[1] | 250.5 μg (5 μM) |
| AMP[1] | 69.44 mg (2 mM) |

2. *Mycoplasma* Substrate (MS) per 100 ml

| | |
|---|---|
| Acetyl phosphate[1] | 55.23 mg (3 mM) |
| Carbamoyl phosphate[1] | 45.87 mg (3 mM) |

3. *Mycoplasma* Assay Buffer (MAB) per 100 ml

| | |
|---|---|
| HEPES[1] | 1.1915 g (50 mM) |
| EDTA[1] | 74.44 mg (2 mM) |
| Triton X-100[1] | 250 μl (0.25%) |
| pH 7.50 | |

Preferred concentration ranges:
ADP 1 μM to 100 mM
AMP 1 μM to 100 mM
Acetyl phosphate 1 μM to 100 mM, preferably, mM to 10 mM
Carbamoyl phosphate 1 μM to 100 mM Suppliers
1.
Sigma-Aldrich Company Ltd.
Fancy Road
Poole
Dorset
BH12 4QH
United Kingdom
2.
Resem BV
Goudenregenstraat 84
NL-4131 BE Vanen
Netherlands
3.
Lucigen Ltd
Porton Down Science Park
Porton, Salisbury
Wiltshire SP4 OJQ
U.K.

The preferred embodiment of the invention provides a selective biochemical test that exploits the activity of certain mycoplasmal enzymes. The presence of these enzymes provides a rapid screening procedure, allowing sensitive detection of contaminating mycoplasma in a test sample. The viable mycoplasma are lysed and the enzymes react with the *Mycoplasma* Substrate catalysing the conversation of ADP to ATP.

By measuring the level of ATP in a sample both before (A) and after (B) the addition of the *Mycoplasma* Substrate, a ratio B/A can be obtained which is indicative of the presence or absence of mycoplasma. If these enzymes are not present, the second reading shows no increase over the first (A), while reaction of mycoplasmal enzymes with their specific substrates in the *Mycoplasma* Substrate Reagent, leads to elevated ATP levels. This increase in ATP can be detected using the following bioluminescent reaction.

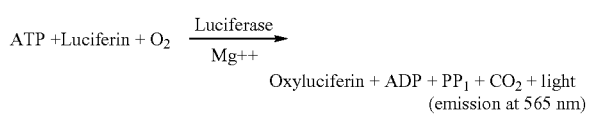

The emitted light intensity is linearly related to the ATP concentration and is measured using a luminometer. The assay is preferably conducted at ambient room temperature (18-22° C.), the optimal temperature for luciferase activity.

Simple Test Protocol of the Invention

Add detection reagent (MDR) to sample
↓
Wait (e.g. 5 mins)
↓
Measure luminescence (Reading A)
↓
Add mycoplasma substrate (MS) to sample
↓
Wait (e.g. 10 mins)
↓
Measure luminescence (Reading B)

If $$\frac{B}{A}$$

is greater than one=mycoplasma contaminated sample.
If $$\frac{B}{A}$$

is one or less=mycoplasma free sample.

Outline of the Method

It is preferred that the culture supernatant be centrifuged to remove cells and, optionally, passed through a bacterial filter prior to performing the assay.

The kit contains all the required reagents to perform the assay.

100 μl of culture supernatant is taken as the sample.
Add *Mycoplasma* detection reagent (MDR)
Wait 5 minutes
Read luminescence (A)
Add *Mycoplasma* Substrate (MS)
Wait 10 minutes.
Read luminescence (B).

Reagent Reconstitution and Storage

Ensure that you follow the correct reagent reconstitution applicable to the relevant kit (10, 25 or 100 assay points).

This procedure usually requires at least 15 minutes equilibration time.

The *Mycoplasma* Detection Reagent (MDR) and *Mycoplasma* Substrate (MS) are preferably supplied as lyophilised pellets. These are reconstituted in *Mycoplasma* Assay Buffer (MAB) to produce the working solutions for use in the assay.

For 10 tests (KIT LT07-118):

1. Preparation of *Mycoplasma* Detection Reagent

Add 600 μl of *Mycoplasma* Assay Buffer into a vial containing the lyophilised *Mycoplasma* Detection Reagent.
Replace the cap and mix gently.
Allow the reagent to equilibrate for 15 minutes at room temperature.

2. Preparation of *Mycoplasma* Substrate

Add 600 μl of *Mycoplasma* Assay Buffer into a vial containing the lyophilised *Mycoplasma* Substrate.
Replace the cap and mix gently.
Allow the reagent to equilibrate for 15 minutes at room temperature.

3. *Mycoplasma* Assay Buffer

This is preferably provided ready for use. Store at 2-8° C. when not in use.

For 25 tests (KIT LT07-218)

1. Preparation of *Mycoplasma* Detection Reagent

Add 600 μl of *Mycoplasma* Assay Buffer into a vial containing the lyophilised *Mycoplasma* Detection Reagent.
Replace the cap and mix gently.
Allow the reagent to equilibrate for 15 minutes at room temperature.

2. Preparation of *Mycoplasma* Substrate

Add 600 μl of *Mycoplasma* Assay Buffer into a vial containing the lyophilised *Mycoplasma* Substrate.
Replace the cap and mix gently.
Allow the reagent to equilibrate for 15 minutes at room temperature.

3. *Mycoplasma* Assay Buffer

This is preferably provided ready for use. Store at 2-8 when not in use.

For 100 tests (KIT LT07-318)

1. Preparation of *Mycoplasma* Detection Reagent

Add 10 ml of *Mycoplasma* Assay Buffer into a vial containing the lyophilised *Mycoplasma* Detection Reagent.
Replace the cap and mix gently.
Allow the reagent to equilibrate for 15 minutes at room temperature.

2. Preparation of *Mycoplasma* Substrate

Add 600 μl of *Mycoplasma* Assay Buffer into a vial containing the lyophilised *Mycoplasma* Substrate.
Replace the cap and mix gently.
Allow the reagent to equilibrate for 15 minutes at room temperature.

3. *Mycoplasma* Assay Buffer

This is preferably provided ready for use. Store at 2-8 when not in use.

Equipment

1. Instrumentation

The kit requires the use of a luminometer. The parameters of the luminometer should be assessed and the conditions below used to produce the correct programming of the machine.

The preferred assay of the invention has been designed for use with cuvette/tube luminometers. For use with plate luminometers please see below.

Cuvette/tube luminometers:
Read time 1 second (integrated).

2. Additional equipment and consumables
a. 10 ml sterile pipettes
b. Luminometer cuvettes
c. Micropipettes—50-200 μl; 200-1000 μl
d. Bench centrifuge.

Preferred Test Protocol

Please note samples of the culture medium should be taken before any further processing steps, e.g. trypsinisation.

1. Bring all reagents up to room temperature before use.
2. Reconstitute the *Mycoplasma* Detection Reagent and *Mycoplasma* Substrate in *Mycoplasma* Assay Buffer. Leave for 15 minutes at room temperature to ensure complete rehydration.
3. Transfer 2 ml of cell culture or culture supernatant into a centrifuge tube and pellet any cells at 1500 rpm (200×g) for 5 minutes.
4. Transfer 100 μl of cleared supernatant into a luminometer cuvette/tube.
5. Program the luminometer to take a 1 second integrated reading (this is usually the default setting on most cuvette luminometers).
6. Add 100 μl of *Mycoplasma* Detection Reagent to each sample and wait 5 minutes.
7. Place cuvette in luminometer and initiate the programme (Reading A).
8. Add 100 μl of *Mycoplasma* Substrate to each sample and wait 10 minutes.
9. Place cuvette in luminometer and initiate the programme (Reading B).
10. Calculate ration=Reading B/Reading A.

Interpretation of Results

The ratio of Reading B to Reading A is used to determine whether a cell culture is contaminated by mycoplasma.

The speed and convenience offered by the kits according to the invention means that it provides a unique method for screening cultures for the presence of mycoplasma. As such it is ideally suited to routine testing of cells in culture. Frequent use of the test methods of the invention will indicate when a cell line becomes infected allowing prompt remedial action to be taken. The test methods of the invention can also be extended to incoming cell lines and the commonly used constituents of complete media.

The interpretation of the different ratios obtained, within each experimental situation, may vary according to the cell types and conditions used.

However, the test gives ratios $$\frac{B}{A}$$

of less than 1 with uninfected cultures.

Cells which are infected with mycoplasma will routinely produce ratios greater than 1.

TABLE A

Interpretation of assay results: illustrating examples of healthy and infected cell lines.

| Cell Line | Mycoplasma ratio | Conclusions |
|---|---|---|
| Infected cells | | |
| K562 | 123.26 | Positive |
| A549 | 4.10 | Positive |
| U937 | 8.26 | Positive |
| HepG2 | 1.27* | Borderline, quarantine and retest in 24 hours |
| Healthy cells | | |
| HL60 | 0.72 | Negative |
| COS-7 | 0.46 | Negative |

Protocol for Plate Luminometers
1. Bring all reagents up to room temperature before use.
2. Reconstitute the *Mycoplasma* Detection Reagent and *Mycoplasma* Substrate in *Mycoplasma* Assay Buffer. Leave for 15 minutes at room temperature to ensure complete rehydration.
3. Transfer 2 ml of cell culture of cell culture supernatant into a centrifuge tube and pellet any cells at 1500 rpm (200×g) for 5 minutes.
4. Transfer 100 μl of cleared supernatant into a luminescence compatible plate.
5. Program the luminometer to take a 1 second integrated reading.
6. Add 100 μl of *Mycoplasma* Detection Reagent to each sample and wait 5 minutes.
7. Place plate in luminometer and initiate the programme (ReadingA).
8. Add 100 μl of *Mycoplasma* Substrate to each sample and wait 10 minutes.
9. Place plate in luminometer and initiate the programme (Reading B).
10. Calculate ratio=Reading B/Reading A.

Great care should be taken when handling any of the reagents. Skin has high levels of ATP on its surface that can contaminate the reagents leading to falsely high readings. Latex gloves avoid this problem.

The optimal working temperature for all reagents is 22° C. If reagents have been refrigerated always allow time for them to reach room temperature (18-22° C.) before use.

The sensitivity of the assay does allow for detection of covert contamination, and if the ratio is marginally above 1 (for example up to 1.3) it is recommended that the sample be retested. Any cultures maintained in quarantine can be tested after a further 24-48 hours in culture to see if the ratios have increased.

SUMMARY

The assays of the invention can be performed in the presence or absence of cells. Unlike known mycoplasma detection systems, they allow for samples to be screened rapidly using cheap hand-held luminometer systems, and can give results within 15 minutes to allow for the appropriate handling of the contaminated samples.

PCR and DAPI/Hoechst staining, will bind to all DNA, be it from viable or non viable mycoplasma. Hence, if looking to treat and remove mycoplasma, you could still end up with false positives when using PCR/DNA staining even though mycoplasma have been irradicated.

The assays can detect viable mycoplasma whereas known methods such as PCR cannot distinguish between viable and non-viable mycoplasma.

REFERENCES

1) Razin S, Yogev D and Naot Y. 1998. Molecular biology and pathogenicity of mycoplasmas. Microbiol. and Mol. Biol. Rev. 62(4): 1094-1156.
2) Rottem S and Barile M F. 1993. Beware of mycopaslasmas. TIBTECH. 11: 143-151.
3) Rottem S. 2002. Sterols and acylated proteins in mycoplasmas. Biochem. Biophys. Res. Commun. 292: 1289-1292.
4) McGarrity G J and Kotani H. 1985. in The mycoplasmas Vol IV. (Razin S and Barile M F eds) p. 353-390. Academic Press.
5) Battaglia M, Pozzi D, Grimaldi S and Parasassi T. 1994. Hoecsht 33258 staining for detecting mycoplasma contamination in cell cultures: a method for reducing fluorescence photobleaching. Biotechnic and Histochem. 69: 152-156.
6) Raab L S. 1999. Cultural revolution: mycoplasma testing kits and services. The Scientist. 13 (20): 21-25.
7) Verhoef V, Germain G and Fridland A. 1983. Adenosine phosphorylase activity in mycoplasma-free growth media for mammalian cells. Exp. Cell Res. 149(1): 37-44.
8) Whitaker A M, Windsor G D, Burnett C M and Taylor C H. 1987. A rapid and sensitive method for the detection of mycoplasmas in infected cell cultures using 6-methyl purine deoxyriboside. Dev. Biol. Stand. 66:503-509.
9) Daxboeck F, Krause R and Wenisch C. 2003. Laboratory diagnosis of *Mycoplasma pneumoniae* infection. Clin. Microbiol. Infect. 9(4): 263-73.
10) de Wet J R, Wood K V, DeLuca M, Helinski D R and Subramani S. 1987. Firefly luciferase gene: structure and expression in mammalian cells. Mol. Cell Biol. 7(2): 725-37.
11) Masuda T, Tatsumi H and Nakano E. 1989. Cloning and sequence analysis of cDNA for luciferase of a Japanese firefly, Luciola cruciata. Gene. 77(2): 265-70.
12) Wood K V, Lam Y A, Seliger H H and McElroy W D. 1989. Complementary DNA coding click beetle luciferases can elicit bioluminenscence of different colours. Science. 244 (4905): 700-2.
13) de Wet J R, Wood K V, Helinski D R and DeLuca M. 1986. Cloning firefly luciferase. Methods Enzymol. 133: 3-14.
14) White P J, Squirrell D J, Arnaud P, Lowe C R and Murray J A. 1996. Improved thermostability of the North American firefly luciferase: saturation mutagenesis at position 354. Biochem J. 319(2): 343-50.
15) Baseman J B and Tully J G. 1997. Mycoplasmas: sophisticated, reemerging, and burdened by their notoriety. Emerg. Infect. Dis. 3(1): 21-32.
16) Kirchhoff H, Mohan K, Schmidt R, Runge M, Brown D R, Brown M B, Foggin C M, Muvavarirwa P, Lehmann H and Flossdorf J. 1997. *Mycoplasma crocodyli* sp. nov., a new species from crocodiles. Int. J. Syst. Bacteriol. 47: 742-6.
17) Forsyth M H, Tully J G, Gorton T S, Hinkley L, Frasca S, van Kruiningen H J and Geary S J. Int. J. Syst. Bacteriol. 1996. *Mycoplasma sturni* sp. nov., from the conjunctiva of a European starling (Sturnus vulgaris). Int. J. Syst. Bacteriol. 46: 716-9.
18) Taylor R R, Mohan K and Miles R J. 1996. Diversity of energy-yielding substrates and metabolism in avian mycoplasmas. Vet. Microbiol. 51: 291-304.
19) Tully J G, Whitcomb R F, Rose D L, Bove J M, Carle P, Somerson N L, Williamson D L and Eden-Green S. 1994. *Acholeplasma brassica* sp. nov. and *Acholeplasma palmae* sp. nov., two non-sterol-requiring mollicutes from plant surfaces. Int. J. Syst. Bacteriol. 44:690-4.
20) Web reference: www.unc.edu/depts/tcf/mycoplasma.htm
21) Duffy L B, Crabb D, Searcey K and Kempf M C. 2000. Comparative potency of gemifloxacin, new quinolones, macrolides, tetracycline and clindamycin against *Mycoplasma* spp. J. Antimicrobial Chemotherapy. 45: 29.
22) Taylor-Robinson D and Bebear C. 1997. Antibiotic susceptibilities of mycoplasmas and treatment of mycoplasmal infections. 40: 622-630.
23) Uphoff C C, Meyer C and Drexler H G. 2002. Elimination of mycoplasma from leukaemia-lymphoma cell lines using antibiotics. 16(2): 284-288.
24) Schram E and Weyens-van Witzenburg A. 1989. Improved ATP methodology for biomass assays. J. Biolumin. Chemilumin. 4: 390-398.
25) Stanley P E. 1989. A review of bioluminescent ATP techniques in rapid microbiology. J. Biolumin. Chemilumin. 4:375-380.
26) Pellegrini A, Thomas U, von Fellenberg R and Wild P. 1992. Bactericidal activities of lysozyme and aprotinin against gram-negative and gram positive bacteria related to their basic character. J. Appl. Bacteriol. 72: 180-187.

The invention claimed is:

1. A method of detecting the presence of potential contaminating mycoplasma in a test sample not known to contain mycoplasma comprising:
   (i) providing the test sample;
   (ii) detecting and/or measuring the activity of an enzyme selected from the group consisting of acetate kinase, carbamate kinase, and a mixture thereof in the test sample, and said activity being indicative of the presence of potential contaminating mycoplasma; and
   (iii) identifying the test sample as potentially contaminated with mycoplasma on the basis of detection and/or measurement of said activity in step (ii).

2. The method of claim 1 further comprising the following steps performed after step (ii) but before step (iii):
   (iia) obtaining enzyme activity information of an enzyme selected from the group consisting of acetate kinase, carbamate kinase and a mixture thereof, detected and/or measured in a corresponding control sample; and
   (iib) comparing the activity detected and/or measured in the test sample in step (ii) of claim 1 with the activity detected and/or measured in the control sample in step (iia); wherein the test sample is identified as potentially contaminated with mycoplasma in step (iii) if the activity detected and/or measured in the test sample in step (ii) is greater than the activity detected and/or measured in the control sample in step (iia), that is, the ratio of the activity detected and/or measured in the test sample in step (ii) to the activity detected and/or measured in the control sample in step (iia) is greater than one.

3. The method of claim 2 wherein the control sample has been shown to be free from mycoplasma by a separate method.

4. The method of claim 3 wherein the control sample has been shown to be free from mycoplasma by one or more of PCR testing, DNA fluorescence staining, or mycoplasma culture method.

5. The method of claim 1 or 2 wherein detecting and/or measuring the activity of an enzyme selected from the group consisting of acetate kinase, carbamate kinase and a mixture thereof in the test sample in step (ii) and/or obtaining enzyme activity information of an enzyme selected from the group consisting of acetate kinase, carbamate kinase and a mixture thereof in a corresponding control sample in step (iia) comprises detecting and/or measuring the appearance and/or disappearance of one or more of the substrates and/or one or more of the products of the following reactions:

$$\text{acetyl phosphate} + \text{ADP} \xrightleftharpoons{\text{acetate kinase}} \text{acetate} + \text{ATP} \quad \text{(Ri)}$$

$$\text{carbamoyl phosphate} + \text{ADP} \xrightleftharpoons{\text{carbamate kinase}} \text{ammonia} + \text{carbonate} + \text{ATP}. \quad \text{(Rii)}$$

6. The method of claim 5 further comprising the step of releasing mycoplasma cellular contents into the sample by treatment of the test sample with a mycoplasma lysis agent that is performed after step (i) but before step (ii).

7. The method of claim 6 wherein the lysis agent is a detergent.

8. The method of claim 7 wherein the detergent lysis treatment is not capable of lysing bacterial cells.

9. The method of claim 8 wherein the corresponding control sample is the same as the test sample prior to mycoplasma lysis treatment.

10. The method of claim 2 wherein the corresponding control sample is the same as the test sample but the step of obtaining detection/measurement for the test sample activity information is carried out after a time interval following the step of obtaining detection/measurement information for the control sample.

11. The method of claim 10 wherein the time interval is at least approximately 30 minutes.

12. The method of claim 1 or 2 wherein the detecting and/or measuring step comprises detecting and/or measuring ATP.

13. The method of claim 12 wherein the ATP is detected and/or measured by a light-emitting reaction.

14. The method of claim 13 where the light emitting reaction is a bioluminescent reaction.

15. The method of claim 12 wherein ADP is added to the test sample prior to the detecting and/or measuring step (ii).

16. The method of claim 15 wherein the control sample is all or an aliquot of the test sample to which a mycoplasma reagent has not been added.

17. The method of claim 12 wherein the control sample has been shown to be free from mycoplasma by a separate method.

18. The method of claim 17 wherein the control sample has been shown to be free from mycoplasma by one or more of PCR testing, DNA fluorescence staining, or mycoplasma culture method.

19. The method of claim 1 or 2 wherein a mycoplasma substrate (MS) reagent is added to the test sample prior to the detecting and/or measuring step (ii).

20. The method of claim 19 wherein the control sample is all or an aliquot of the test sample to which a mycoplasma reagent has not been added.

21. The method of claim 19 wherein the control sample has been shown to be free from mycoplasma by a separate method.

22. The method of claim 21 wherein the control sample has been shown to be free from mycoplasma by one or more of PCR testing, DNA fluorescence staining, or mycoplasma culture method.

23. The method of claim 19 wherein the MS reagent is selected from the groups consisting of acetyl phosphate, a precursor of acetyl phosphate, carbamoyl phosphate and a precursor of carbamoyl phosphate.

24. The method of claim 23 wherein the precursor of acetyl phosphate is acetyl-CoA.

25. The method of claim 23 wherein the precursor of carbamoyl phosphate is selected from the group consisting of citrulline, ammonia and a mixture thereof.

26. The method of claim 1 or 2 wherein the test sample and/or control sample is a cell-culture sample.

27. The method of claim 26 wherein cells in the cell-culture sample are mammalian cells.

28. The method of claim 27 wherein the mammalian cells in the cell-culture sample grow in suspension.

29. The method of claim 28 wherein the cells are selected from the group consisting of K562, U937, HL-60, Cem-7, Jurkats and leukaemic blast cells.

30. The method of claim 27 wherein the mammalian cells are adherent cells or adherent primary cells isolated from an animal source.

31. The method of claim 30 wherein the cells are selected from Vero, MRC5, HUVEC, BSMC, NHEK, MCF-7, AoSMC, A549, HepG2, FM3A, PC12, ARPE-19, CHO and COS cells.

32. The method of claim 26 where the cell culture is a culture of plant cells.

33. The method of claim 26 where the cell culture sample is a sample which is derived from a cell culture but is itself substantially free of cellular material.

34. The method of claim 26 where the cell culture is a culture of insect cells.

35. The method of claim 1 or 2 wherein the test sample and/or control sample consists of a cell-free reagent.

36. The method of claim 35 where the cell-free reagent is trypsin.

37. A process for treating a cell culture to remove potential mycoplasma contamination comprising: treating a potentially mycoplasma contaminated cell culture with an agent to remove and/or destroy mycoplasma; and subsequently testing a sample from the culture for potential mycoplasma contamination using the method of claim 1 or 2; if necessary, repeating the process of treating one or more times until mycoplasma contamination is not detected in a sample.

38. A method of detecting the presence of potential mycoplasma in a test sample not known to contain mycoplasma, comprising the following steps:
    (i) providing the test sample;
    (ii) without adding an exogenous reagent (e.g. substrates for kinase activity) to convert ADP to ATP, detecting or measuring ATP in the test sample using a bioluminescent reaction to obtain an ATP and/or light output measurement;
    (iii) obtaining an ATP and/or light output measurement from a corresponding control sample;
    (iv) determining the ATP and/or light output measurement ratio as (ATP and/or light output measurement from the corresponding control sample)/(ATP and/or light measurement from the test sample); and
    (v) identifying the test sample as potentially contaminated with mycoplasma in the event that the ratio of (ATP and/or light output measurement from the corresponding control sample)/(ATP and/or light measurement from the test sample) is greater than one.

39. The method of claim 1, 2 or 38 wherein the method includes a step of passing the test sample through a filter which retains bacterial cells.

40. A method of detecting the presence of potential contaminating mycoplasma in a test sample not known to contain mycoplasma comprising:
    (i) providing the test sample;
    (ii) treating the test sample under a condition sufficient to lyse potential contaminating mycoplasma but insufficient to lyse bacterial cells;
    (iii) detecting and/or measuring the activity of an enzyme selected from the group consisting of acetate kinase, carbamate kinase, and a mixtur thereof in the test sample, and said activity being indicative of the presence of potential contaminating mycoplasma; and
    (iv) identifying the test sample as potentially contaminated with mycoplasma on the basis of detection and/or measurement of said activity in step (iii).

41. A method of detecting the presence of potential mycoplasma in a test sample not known to contain mycoplasma, comprising the following steps:
    (i) providing the test sample;
    (ii) treating the test sample under a condition sufficient to lyse potential contaminating mycoplasma but insufficient to lyse bacterial cells
    (iii) without adding an exogenous reagent (e.g. substrates for kinase activity) to convert ADP to ATP, detecting or measuring ATP in the test sample using a bioluminescent reaction to obtain an ATP and/or light output measurement;
    (iv) obtaining an ATP and/or light output measurement from a corresponding control sample;
    (v) determining the ATP and/or light output measurement ratio as (ATP and/or light output measurement from the corresponding control sample)/(ATP and/or light measurement from the test sample); and
    (vi) identifying the test sample as potentially contaminated with mycoplasma in the event that the ratio of (ATP and/or light output measurement from the corresponding control sample)/(ATP and/or light measurement from the test sample) is greater than one.

42. A method of detecting the presence of potential contaminating mycoplasma in a test sample not known to contain mycoplasma comprising:
    (i) providing the test sample;
    (ii) passing the test sample through a filter which retains bacterial cells;
    (iii) detecting and/or measuring the activity of an enzyme selected from the group consisting of acetate kinase, carbamate kinase, and a mixtur thereof in the test sample, and said activity being indicative of the presence of potential contaminating mycoplasma; and
    (iv) identifying the test sample as potentially contaminated with mycoplasma on the basis of the detection and/or measurement of said activity in step (iii).

43. The method of claim 42, further comprising the following steps performed after step (iii) but before step (iv):
    (iiia) obtaining enzyme activity information of an enzyme selected from the group consisting of acetate kinase, carbamate kinase and a mixture thereof; detected and/or measured in a corresponding control sample; and
    (iiib) comparing the activity detected and/or measured in the test sample in step
    (iii) of claim 42 with the activity detected and/or measured in the control sample in step (iiia);
    wherein the test sample is identified as potentially contaminated with mycoplasma in step (iv) if the activity detected and/or measured in the test sample in step (iii) of claim 1 with the activity detected and/or measured in the control sample in step (iiia), that is, the ration of the activity detected and/or measured in the test sample in step (iii) to the activity detected and/or measured in the control sample in step (iiia) is greater than one.

44. The method of claim 42 or 43 wherein detecting and/or measuring the activity of an enzyme selected from the group consisting of acetate kinase, carbamate kinase and a mixture thereof in the test sample in step (iii) and/or obtaining enzyme activity information of an enzyme selected from the group consisting of acetate kinase, carbamate kinase and a mixture thereof in a corresponding control sample in step (iiia) comprises detecting and/or measuring the appearance and/or disappearance of one or more of the substrates and/or one or more of the products of the following reactions:

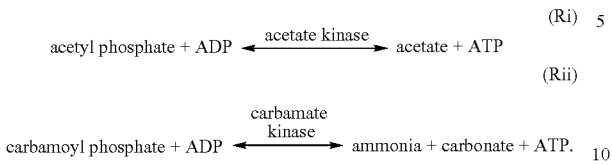

45. A method of detecting the potential presense of mycoplasma in a test sample not known to contain mycoplasma comprising the following steps:
 (i) providing the test sample;
 (ii) passing the test sample through a filter which retains bacterial cells;
 (iii) without adding an exogenous reagent (e.g. substrates for kinase activity) to convert ADP to ATP, detecting or measuring ATP in the test sample using a bioluminescent reaction to obtain an ATP and/or light output measurement;
 (iv) obtaining an ATP and/or light output measurement from a corresponding control sample;
 (v) comparing the ATP and/or light output measurement ration as (ATP and/or light output measurement from the corresponding control sample)/(ATP and/or light measurement from the tests sample); and
 (vi) identifying the test sample as potentially contaminated with mycoplasma in the vent that the ratio of (ATP and/or light output measurement from the corresponding control sample)/(ATP and/or light measurement from the test sample) is greater than one.

* * * * *